US010435757B1

(12) United States Patent
Totary-Jain et al.

(10) Patent No.: US 10,435,757 B1
(45) Date of Patent: Oct. 8, 2019

(54) METHODS OF MEASURING C19MC MIRNA IN A POST-NATAL TISSUE AND USES THEREOF

(71) Applicants: Hana Totary-Jain, Wesley Chapel, FL (US); Ezinne Francess Mong, Tampa, FL (US)

(72) Inventors: Hana Totary-Jain, Wesley Chapel, FL (US); Ezinne Francess Mong, Tampa, FL (US)

(73) Assignee: University of South Florida, Tampa, FL (US)

( * ) Notice: Subject to any disclaimer, the term of this patent is extended or adjusted under 35 U.S.C. 154(b) by 49 days.

(21) Appl. No.: 15/623,832

(22) Filed: Jun. 15, 2017

Related U.S. Application Data

(60) Provisional application No. 62/350,232, filed on Jun. 15, 2016.

(51) Int. Cl.
| | | |
|---|---|---|
| *C12Q 1/6886* | (2018.01) | |
| *C12Q 1/6883* | (2018.01) | |
| *A61K 48/00* | (2006.01) | |
| *C12N 15/11* | (2006.01) | |

(52) U.S. Cl.
CPC .......... *C12Q 1/6886* (2013.01); *A61K 48/005* (2013.01); *C12N 15/11* (2013.01); *C12Q 1/6883* (2013.01); *C12N 2310/20* (2017.05); *C12Q 2600/154* (2013.01); *C12Q 2600/158* (2013.01); *C12Q 2600/178* (2013.01)

(58) Field of Classification Search
CPC .............. C12N 15/111; C12N 2310/14; A61K 31/713; A61K 48/0033
USPC ...... 435/6.1, 6.11, 91.1, 91.31, 455; 514/44; 536/23.1, 24.5
See application file for complete search history.

(56) References Cited

U.S. PATENT DOCUMENTS

| | | |
|---|---|---|
| 9,242,000 B2 | 1/2016 | Cheresh et al. |
| 2014/0127284 A1 | 5/2014 | Cheresh et al. |
| 2015/0352186 A1 | 12/2015 | Wollert et al. |

FOREIGN PATENT DOCUMENTS

WO        2012052953        4/2012

OTHER PUBLICATIONS

Mouillet et al (Am. J. of Obstetrics and Gynec., Oct. 2015, S163-S-172) (Year: 2015).*
Stub, Graham M., et al. "Endothelial and circulating C19MC microRNAs are biomarkers of infantile hemangioma." JCI insight 1.14 (2016).
Bertoni, Natália, et al. "Integrative meta-analysis identities microRNA-regulated networks in infantile hemangioma." BMC medical genetics 17.1 (2016): 4.
A. N. Haggstrom, et al., "Prospective Study of Infantile Hemangiomas: Demographic, Prenatal, and Perinatal Characteristics," J. Pediatr., vol. 150, pp. 291-294, 2007.
Ritter, M. R., et al. "Pathogenesis of infantile haemangioma: new molecular and cellular insights.," vol. 9, No. 32, pp. 1-19, 2007.
Itinteang, Tinte, et al, "A placental chorionic villous mesenchymal core cellular origin for infantile haemangioma." Journal of clinical pathology 64.10 (2011): 870-874.
Léauté-Labrèze, Christine, et al. "A randomized, controlled trial of oral propranolol in infantile hemangioma." New England Journal of Medicine 372.8 (2015): 735-746.
Small, Eric M., and Eric N. Olson. "Pervasive roles of microRNAs in cardiovascular biology." Nature 469.7330 (2011): 336-342.
Noguer-Dance, Marie, et al. "The primate-specific microRNA gene cluster (C19MC) is imprinted in the placenta." Human molecular genetics 19.18 (2010): 3566-3582.
Mouillet, Jean-François, et al. "MicroRNAs in placental health and disease." American journal of obstetrics and gynecology 213.4 (2015): S163-S172.
Kleinman, Mark E., et al. "Hypoxia-induced mediators of stem/progenitor cell trafficking are increased in children with hemangioma." Arteriosclerosis, thrombosis, and vascular biology 27.12 (2007): 2664-2670.
Liu, Quanyan, et al. "Hypoxia induces genomic DNA demethylation through the activation of HIF-1α and transcriptional upregulation of MAT2A in hepatoma cells." Molecular cancer therapeutics (2011)., vol. 10, No. 6, pp. 1113-1123.
Hartley, Iain, et al. "Long-lasting changes in DNA methylation following short-term hypoxic exposure in primary hippocampal neuronal cultures." PloS one 8.10 (2013): e77859.
Konermann, Silvana, et al. "Genome-scale transcriptional activation by an engineered CRISPR-Cas9 complex." Nature 517.7536 (2014): 583.
Calicchio, Monica L., Tucker Collins, and Harry R Kozakewich. "Identification of signaling systems in proliferating and involuting phase infantile hemangiomas by genome-wide transcriptional profiling." The American journal of pathology 174.5 (2009): 1638-1649.
Schultz, Brent, et al. "A common polymorphism within the IGF2 imprinting control region is associated with parent of origin specific effects in infantile hemangiomas." PloS one 10.10 (2015): e0113168.
North, Paula E., et al. "A unique microvascular phenotype shared by juvenile hemangiomas and human placenta." Archives of dermatology 137.5 (2001): 559-570.
López Gutiérrez, Juan Carlos, et al. "Placental anomalies in children with infantile hemangioma." Pediatric dermatology 24.4 (2007): 353-355.

(Continued)

*Primary Examiner* — Jane J Zara
(74) *Attorney, Agent, or Firm* — Thomas|Horstemeyer, LLP

(57) ABSTRACT

Provided herein are methods of measuring C19MC miRNA amount and/or expression in a post-natal cell and/or tissue. Provided herein are methods of measuring CpG methylation of the upstream C19MC miRNA promoter region in a post-natal cell and/or tissue. Also provided herein are methods of treating a cell, population thereof, and/or a subject in need thereof by administering a C19MC miRNA inhibitor or CRISPR to suppress the expression of specific miRNA within the C19MC or the entire C19MC cluster, population thereof, and/or the subject in need thereof.

6 Claims, 4 Drawing Sheets

Specification includes a Sequence Listing.

(56) References Cited

OTHER PUBLICATIONS

Léeauté-Labrèze, Christine, et al. "Propranolol for severe hemangiomas of infancy." New England Journal of Medicine 358.24 (2008): 2649-2651.
Storch, C. H., and P. H. Hoeger. "Propranolol for infantile haemangiomas: insights into the molecular mechanisms of action." British Journal of Dermatology 163.2 (2010): 269-274.
Mansouri, Parvin, et al. "Propranolol in infantile hemangioma: a review article." Journal of Skin and Stem Cell 1.2 (2014): 1-5.
Drut, R. M., and R. Drut. "Extracutaneous infantile haemangioma is also Glut1 positive." Journal of clinical pathology 57.11 (2004): 1197-1200.
Barnés, Carmen M., et al. "Evidence by molecular profiling for a placental origin of infantile hemangioma." Proceedings of the National Academy of Sciences 102.52 (2005): 19097-19102.
Khan, Zia A., et al. "Multipotential stem cells recapitulate human infantile hemangioma in immunodeficient mice." The Journal of clinical investigation 118.7 (2008): 2592-2599.
Wei, Liang, et al. "Construction of recombinant adenovirus vector containing a modified gene that codes for human hypoxia-inducible factor-1α without oxygen-dependent degradation domain." Plasmid 63.1 (2010): 20-26.
Yuan, Yong, et al. "Cobalt inhibits the interaction between hypoxia-inducible factor-α and von Hippel-Lindau protein by direct binding to hypoxia-inducible factor-α." Journal of Biological Chemistry 278.18 (2003): 15911-15916.
Agarwal, Vikram, et al. "Predicting effective microRNA target sites in mammalian mRNAs." elife 4 (2015): e05005.
Wang, Jing, et al. "WEB-based gene set analysis toolkit (WebGestalt): update 2013." Nucleic acids research 41.W1 (2013): W77-W83.
Zhang,Bing, Stefan Kirov, and Jay Snoddy. "WebGestalt: an integrated system for exploring gene sets in various biological contexts." Nucleic acids research 33.suppl_2 (2005): W741-W748.
Liu, Xiaojun, et al. "PTPN14 interacts with and negatively regulates the oncogenic function of YAP." Oncogene 32.10 (2013): 1266-1273.
Wang, Wenqi, et al. "PTPN14 is required for the density-dependent control of YAP1." Genes & development 26.17 (2012): 1959-1971.
Meng, Zhipeng, Toshiro Moroishi, and Kun-Liang Guan. "Mechanisms of Hippo pathway regulation." Genes & development 30.1 (2016): 1-17.
Lewis, Benjamin P., Christopher B. Burge, and David P. Bartel. "Conserved seed pairing, often flanked by adenosines, indicates that thousands of human genes are microRNA targets." cell 120.1 (2005): 15-20.
Lin, Sheng, et al. "Computational identification and characterization of primate-specific microRNAs in human genome." Computational biology and chemistry 34.4 (2010): 232-241.
Delorme-Axford, Elizabeth, et al. "Human placental trophoblasts confer viral resistance to recipient cells." Proceedings of the National Academy of Sciences 110.29 (2013): 12048-12053.

* cited by examiner

SEQUENCE LISTING

```
<160> NUMBER OF SEQ ID NOS: 97

<210> SEQ ID NO 1
<211> LENGTH: 90
<212> TYPE: RNA
<213> ORGANISM: Artificial Sequence
<220> FEATURE:
<223> OTHER INFORMATION: miR-516a

<400> SEQUENCE: 1
ucucaggcug ugaccuucuc gaggaaagaa gcacuuucug uugucugaaa gaaaagaaag    60
ugcuuccuuu cagagggnua cgguuugaga                                    90

<210> SEQ ID NO 2
<211> LENGTH: 101
<212> TYPE: RNA
<213> ORGANISM: Artificial Sequence
<220> FEATURE:
<223> OTHER INFORMATION: miR-518c

<400> SEQUENCE: 2
gcgagaagau cucaugcugu gacucucugg agggaagcac uuucuguugu cugaaagaaa    60
acaaagcgcu ucucuuuaga guguuacggu uugagaaaag c                      101

<210> SEQ ID NO 3
<211> LENGTH: 87
<212> TYPE: RNA
<213> ORGANISM: Artificial Sequence
<220> FEATURE:
<223> OTHER INFORMATION: miR-517a

<400> SEQUENCE: 3
ucucaggcag ugacccucua gauggaagca cugucuguug uauaaaagaa aagaucgugc    60
aucccuuuag aguguuacug uuugaga                                       87

<210> SEQ ID NO 4
<211> LENGTH: 85
<212> TYPE: RNA
<213> ORGANISM: Artificial Sequence
<220> FEATURE:
<223> OTHER INFORMATION: miR-519a-1

<400> SEQUENCE: 4
cucaggcugu gacacucuag agggaagcgc uuucuguugu cugaaagaaa ggaaagugca    60
uccuuuuaga guguuacugu uugag                                         85

<210> SEQ ID NO 5
<211> LENGTH: 83
<212> TYPE: RNA
<213> ORGANISM: Artificial Sequence
<220> FEATURE:
<223> OTHER INFORMATION: miR-515-1

<400> SEQUENCE: 5
ucucaugcag ucauucucca aaagaaagca cuuucuguug ucugaaagca gagugccuuc    60
uuuuggagcg uuacuguuug aga                                           83

<210> SEQ ID NO 6
<211> LENGTH: 90
<212> TYPE: RNA
<213> ORGANISM: Artificial Sequence
<220> FEATURE:
<223> OTHER INFORMATION: miR-516b-1
```

<400> SEQUENCE: 6
ucucaggcug ugaccaucug gagguaagaa gcacuuucug uuuugugaaa gaaaagaaag    60
ugcuuccuuu cagagggüua cucuuugaga    90

<210> SEQ ID NO 7
<211> LENGTH: 83
<212> TYPE: RNA
<213> ORGANISM: Artificial Sequence
<220> FEATURE:
<223> OTHER INFORMATION: miR-518b

<400> SEQUENCE: 7
ucaugcugug gcccuccaga gggaagcgcu uucuguuguc ugaagaaaaa caaagcgcuc    60
cccuuuagag guuuacgguu uga    83

<210> SEQ ID NO 8
<211> LENGTH: 88
<212> TYPE: RNA
<213> ORGANISM: Artificial Sequence
<220> FEATURE:
<223> OTHER INFORMATION: miR-518e

<400> SEQUENCE: 8
ucucaggcug ugacccucua gagggaagcg cuuucuguug gcuaaaagaa aagaaagcgc    60 uuccccuucag aguguuaacg cuuugaga    88

<210> SEQ ID NO 9
<211> LENGTH: 85
<212> TYPE: RNA
<213> ORGANISM: Artificial Sequence
<220> FEATURE:
<223> OTHER INFORMATION: miR-518a-1

<400> SEQUENCE: 9
ucucaagcug ugacugcaaa gggaagcccu uucuguuguc ugaagaaga gaaagcgcuu    60 cccuuugcug gauuacgguu ugaga    85

<210> SEQ ID NO 10
<211> LENGTH: 83
<212> TYPE: RNA
<213> ORGANISM: Artificial Sequence
<220> FEATURE:
<223> OTHER INFORMATION: miR-515-2

<400> SEQUENCE: 10
ucucaugcag ucauucucca aaagaaagca cuuucguug ucugaaagca gagugccuuc    60
uuuuggagcg uuacuguuug aga    83

<210> SEQ ID NO 11
<211> LENGTH: 84
<212> TYPE: RNA
<213> ORGANISM: Artificial Sequence
<220> FEATURE:
<223> OTHER INFORMATION: miR-512-1

<400> SEQUENCE: 11
ucucagucug uggcacucag ccuugagggc acuuucuggu gccagaauga aagugcuguc    60
auagcugagg uccaaugacu gagg    84

<210> SEQ ID NO 12

```
<211> LENGTH: 87
<212> TYPE: RNA
<213> ORGANISM: Artificial Sequence
<220> FEATURE:
<223> OTHER INFORMATION: miR-518f

<400> SEQUENCE: 12
ucucaugcug ugacccucua gagggaagca cuuucucuug ucuaaaagaa aagaaagcgc      60
uucucuuuag aggauuacuc uuugaga                                         87

<210> SEQ ID NO 13
<211> LENGTH: 87
<212> TYPE: RNA
<213> ORGANISM: Artificial Sequence
<220> FEATURE:
<223> OTHER INFORMATION: miR-1283-1

<400> SEQUENCE: 13
cucaagcuau gagucuacaa aggaaagcgc uuucuguugu cagaaagaag agaaagcgcu     60
ucccuuuuga ggguuacggu uugagaa                                        87

<210> SEQ ID NO 14
<211> LENGTH: 88
<212> TYPE: RNA
<213> ORGANISM: Artificial Sequence
<220> FEATURE:
<223> OTHER INFORMATION: miR-519d

<400> SEQUENCE: 14
ucccaugcug ugacccucca aagggaagcg cuuucuguuu guuucucuu aaacaaagug      60 ccucccuuua gaguguuacc guuuggga                                       88

<210> SEQ ID NO 15
<211> LENGTH: 67
<212> TYPE: RNA
<213> ORGANISM: Artificial Sequence
<220> FEATURE:
<223> OTHER INFORMATION: miR-517b

<400> SEQUENCE: 15
gugacccucu agauggaagc acugucuguu gucuaagaaa agaucgugca ucccuuuaga     60
guguuac                                                              67

<210> SEQ ID NO 16
<211> LENGTH: 87
<212> TYPE: RNA
<213> ORGANISM: Artificial Sequence
<220> FEATURE:
<223> OTHER INFORMATION: miR-521-2

<400> SEQUENCE: 16
ucucgggcug ugacucucca aagggaagaa uuucucuug ucuaaaagaa aagaacgcac      60
uucccuuuag aguguuaccg ugugaga                                        87

<210> SEQ ID NO 17
<211> LENGTH: 87
<212> TYPE: RNA
<213> ORGANISM: Artificial Sequence
<220> FEATURE:
<223> OTHER INFORMATION: miR-524

<400> SEQUENCE: 17
ucucaugcug ugacccuaca aagggaagca cuuucucuug uccaaaggaa aagaaggcgc     60
```

```
uucccuuugg aguguuacgg uuugaga                                    87

<210> SEQ ID NO 18
<211> LENGTH: 90
<212> TYPE: RNA
<213> ORGANISM: Artificial Sequence
<220> FEATURE:
<223> OTHER INFORMATION: miR-520g

<400> SEQUENCE: 18
ucccaugcug ugacccucua gaggaagcac uuucuguuug uugucugaga aaaaacaaag    60
ugcuucccuu uagaguguua ccguuuggga                                    90

<210> SEQ ID NO 19
<211> LENGTH: 85
<212> TYPE: RNA
<213> ORGANISM: Artificial Sequence
<220> FEATURE:
<223> OTHER INFORMATION: miR-525

<400> SEQUENCE: 19
cucaagcugu gacucuccag agggaugcac uuucucuuau gugaaaaaaa agaaggcgcu    60 uccccuuuaga gcguuacggu uuggg                                        85

<210> SEQ ID NO 20
<211> LENGTH: 87
<212> TYPE: RNA
<213> ORGANISM: Artificial Sequence
<220> FEATURE:
<223> OTHER INFORMATION: miR-520d

<400> SEQUENCE: 20
ucucaagcug ugagcuacaa agggaagcc cuuucuguug ucuaaaagaa aagaaagugc    60
uucucuuugg uggguuacgg uuugaga                                       87

<210> SEQ ID NO 21
<211> LENGTH: 83
<212> TYPE: RNA
<213> ORGANISM: Artificial Sequence
<220> FEATURE:
<223> OTHER INFORMATION: miR-526b

<400> SEQUENCE: 21
ucaggcugug acccucuuga gggaagcacu uucuguuguc ugaaagaaga gaaagugcuu    60
ccuuuuagag gcuuacuguc uga                                           83

<210> SEQ ID NO 22
<211> LENGTH: 84
<212> TYPE: RNA
<213> ORGANISM: Artificial Sequence
<220> FEATURE:
<223> OTHER INFORMATION: miR-519e

<400> SEQUENCE: 22
ucucaugcag ucauucucca aaagggagca cuuucuguuu gaaagaaaac aaagugccuc    60
cuuuuagagu guuacuguuu gaga                                          84

<210> SEQ ID NO 23
<211> LENGTH: 73
<212> TYPE: RNA
<213> ORGANISM: Artificial Sequence
<220> FEATURE:
```

```
<223> OTHER INFORMATION: miR-1323

<400> SEQUENCE: 23
acugaggucc ucaaaacuga ggggcauuuu cuguggauug aaaggaaagu gcacccaguu    60
uuggggaugu caa                                                      73

<210> SEQ ID NO 24
<211> LENGTH: 87
<212> TYPE: RNA
<213> ORGANISM: Artificial Sequence
<220> FEATURE:
<223> OTHER INFORMATION: miR-522

<400> SEQUENCE: 24
ucucaggcug ugucccucua gagggaagcg cuuucuguug ucugaaagaa aagaaaaugg    60
uucccuuuag aguguuacgc uuugaga                                       87

<210> SEQ ID NO 25
<211> LENGTH: 87
<212> TYPE: RNA
<213> ORGANISM: Artificial Sequence
<220> FEATURE:
<223> OTHER INFORMATION: miR-519a-2

<400> SEQUENCE: 25
ucucaggcug ugucccucua cagggaagcg cuuucuguug ucugaaagaa aggaaagugc    60
auccuuuuag aguguuacug uuugaga                                       87

<210> SEQ ID NO 26
<211> LENGTH: 85
<212> TYPE: RNA
<213> ORGANISM: Artificial Sequence
<220> FEATURE:
<223> OTHER INFORMATION: miR-520a

<400> SEQUENCE: 26
cucaggcugu gacccuccag agggaaguac uuucuguugu cugagagaaa agaaagugcu    60
ucccuuugga cguuucggu uugag                                          85

<210> SEQ ID NO 27
<211> LENGTH: 85
<212> TYPE: RNA
<213> ORGANISM: Artificial Sequence
<220> FEATURE:
<223> OTHER INFORMATION: miR-527

<400> SEQUENCE: 27
ucucaagcug ugacugcaaa gggaagcccu uucuguuguc uaaaagaaaa gaaagugcuu    60
cccuuuggug aauuacgguu ugaga                                         85

<210> SEQ ID NO 28
<211> LENGTH: 87
<212> TYPE: RNA
<213> ORGANISM: Artificial Sequence
<220> FEATURE:
<223> OTHER INFORMATION: miR-523

<400> SEQUENCE: 28
ucucaugcug ugacccucua gagggaagcg cuuucuguug ucugaaagaa aagaacgcgc    60
uucccuauag agguuaccc uuugaga                                        87
```

```
<210> SEQ ID NO 29
<211> LENGTH: 88
<212> TYPE: RNA
<213> ORGANISM: Artificial Sequence
<220> FEATURE:
<223> OTHER INFORMATION: miR-520h

<400> SEQUENCE: 29
ucccaugcug ugacccucua gaggaagcac uuucuguuug uugucugaga aaaaacaaag     60
ugcuucccuu uagaguuacu guuuggga                                        88

<210> SEQ ID NO 30
<211> LENGTH: 81
<212> TYPE: RNA
<213> ORGANISM: Artificial Sequence
<220> FEATURE:
<223> OTHER INFORMATION: miR-519b

<400> SEQUENCE: 30
caugcuguga cccucuagag ggaagcgcuu ucguugucu gaaagaaaag aaagugcauc       60
cuuuuagagg uuuacuguuu g                                                81

<210> SEQ ID NO 31
<211> LENGTH: 61
<212> TYPE: RNA
<213> ORGANISM: Artificial Sequence
<220> FEATURE:
<223> OTHER INFORMATION: miR-520b

<400> SEQUENCE: 31
cccucuacag ggaagcgcuu ucguugucu gaaagaaaag aaagugcuuc cuuuuagagg       60
g                                                                      61

<210> SEQ ID NO 32
<211> LENGTH: 87
<212> TYPE: RNA
<213> ORGANISM: Artificial Sequence
<220> FEATURE:
<223> OTHER INFORMATION: miR-519c

<400> SEQUENCE: 32
ucucagccug ugacccucua gagggaagcg cuuucguuug ucugaaagaa aagaaagugc     60
aucuuuuuag aggauuacag uuugaga                                         87

<210> SEQ ID NO 33
<211> LENGTH: 87
<212> TYPE: RNA
<213> ORGANISM: Artificial Sequence
<220> FEATURE:
<223> OTHER INFORMATION: miR-520f

<400> SEQUENCE: 33
ucucaggcug ugacccucua aagggaagcg cuuucugugg ucagaaagaa agcaagugc      60 uuccuuuuag aggguuaccg uuuggga                                         87

<210> SEQ ID NO 34
<211> LENGTH: 124
<212> TYPE: RNA
<213> ORGANISM: Artificial Sequence
<220> FEATURE:
<223> OTHER INFORMATION: miR-498

<400> SEQUENCE: 34
```

```
aacccuccuu gggaagugaa gcucaggcug ugauuucaag ccaggggggcg uuuuucuaua    60 acuggaugaa aagcaccucc agagcuugaa gcucacaguu ugagagcaau cgucuaagga   120
aguu                                                                124
```

```
<210> SEQ ID NO 35
<211> LENGTH: 87
<212> TYPE: RNA
<213> ORGANISM: Artificial Sequence
<220> FEATURE:
<223> OTHER INFORMATION: miR-520c

<400> SEQUENCE: 35
ucucaggcug ucguccucua gagggaagca cuuucuguug ucugaaagaa aagaaagugc    60
uuccuuuuag aggguuaccg uuugaga                                        87
```

```
<210> SEQ ID NO 36
<211> LENGTH: 23
<212> TYPE: RNA
<213> ORGANISM: Artificial Sequence
<220> FEATURE:
<223> OTHER INFORMATION: MIMAT0004770

<400> SEQUENCE: 36
uucucgagga aagaagcacu uuc                                            23
```

```
<210> SEQ ID NO 37
<211> LENGTH: 23
<212> TYPE: RNA
<213> ORGANISM: Artificial Sequence
<220> FEATURE:
<223> OTHER INFORMATION: MIMAT0002847

<400> SEQUENCE: 37
ucucuggagg gaagcacuuu cug                                            23
```

```
<210> SEQ ID NO 38
<211> LENGTH: 22
<212> TYPE: RNA
<213> ORGANISM: Artificial Sequence
<220> FEATURE:
<223> OTHER INFORMATION: MIMAT0002851

<400> SEQUENCE: 38
ccucuagaug gaagcacugu cu                                             22
```

```
<210> SEQ ID NO 39
<211> LENGTH: 22
<212> TYPE: RNA
<213> ORGANISM: Artificial Sequence
<220> FEATURE:
<223> OTHER INFORMATION: MIMAT0005452

<400> SEQUENCE: 39
cucuagaggg aagcgcuuuc ug                                             22
```

```
<210> SEQ ID NO 40
<211> LENGTH: 24
<212> TYPE: RNA
<213> ORGANISM: Artificial Sequence
<220> FEATURE:
<223> OTHER INFORMATION: MIMAT0002826

<400> SEQUENCE: 40
uucuccaaaa gaaagcacuu ucug                                           24
```

```
<210> SEQ ID NO 41
<211> LENGTH: 22
<212> TYPE: RNA
<213> ORGANISM: Artificial Sequence
<220> FEATURE:
<223> OTHER INFORMATION: MIMAT0002859

<400> SEQUENCE: 41
aucuggaggu aagaagcacu uu                                              22

<210> SEQ ID NO 42
<211> LENGTH: 22
<212> TYPE: RNA
<213> ORGANISM: Artificial Sequence
<220> FEATURE:
<223> OTHER INFORMATION: MIMAT0005450

<400> SEQUENCE: 42
cucuagaggg aagcgcuuuc ug                                              22

<210> SEQ ID NO 43
<211> LENGTH: 20
<212> TYPE: RNA
<213> ORGANISM: Artificial Sequence
<220> FEATURE:
<223> OTHER INFORMATION: MIMAT0005457

<400> SEQUENCE: 43
cugcaaaggg aagcccuuuc                                                 20

<210> SEQ ID NO 44
<211> LENGTH: 24
<212> TYPE: RNA
<213> ORGANISM: Artificial Sequence
<220> FEATURE:
<223> OTHER INFORMATION: MIMAT0002826

<400> SEQUENCE: 44
uucuccaaaa gaaagcacuu ucug                                            24

<210> SEQ ID NO 45
<211> LENGTH: 23
<212> TYPE: RNA
<213> ORGANISM: Artificial Sequence
<220> FEATURE:
<223> OTHER INFORMATION: MIMAT0002822

<400> SEQUENCE: 45
cacucagccu ugagggcacu uuc                                             23

<210> SEQ ID NO 46
<211> LENGTH: 22
<212> TYPE: RNA
<213> ORGANISM: Artificial Sequence
<220> FEATURE:
<223> OTHER INFORMATION: MIMAT0002841

<400> SEQUENCE: 46
cucuagaggg aagcacuuuc uc                                              22

<210> SEQ ID NO 47
<211> LENGTH: 22
<212> TYPE: RNA
<213> ORGANISM: Artificial Sequence
<220> FEATURE:
```

<223> OTHER INFORMATION: MIMAT0005799

<400> SEQUENCE: 47
ucuacaaagg aaagcgcuuu cu                                    22

<210> SEQ ID NO 48
<211> LENGTH: 22
<212> TYPE: RNA
<213> ORGANISM: Artificial Sequence
<220> FEATURE:
<223> OTHER INFORMATION: MIMAT0002851

<400> SEQUENCE: 48
ccucuagaug gaagcacugu cu                                    22

<210> SEQ ID NO 49
<211> LENGTH: 22
<212> TYPE: RNA
<213> ORGANISM: Artificial Sequence
<220> FEATURE:
<223> OTHER INFORMATION: MIMAT0002849

<400> SEQUENCE: 49
cuacaaaggg aagcacuuuc uc                                    22

<210> SEQ ID NO 50
<211> LENGTH: 21
<212> TYPE: RNA
<213> ORGANISM: Artificial Sequence
<220> FEATURE:
<223> OTHER INFORMATION: MIMAT0002838

<400> SEQUENCE: 50
cuccagaggg augcacuuuc u                                     21

<210> SEQ ID NO 51
<211> LENGTH: 20
<212> TYPE: RNA
<213> ORGANISM: Artificial Sequence
<220> FEATURE:
<223> OTHER INFORMATION: MIMAT0002855

<400> SEQUENCE: 51
cuacaaaggg aagcccuuuc                                       20

<210> SEQ ID NO 52
<211> LENGTH: 23
<212> TYPE: RNA
<213> ORGANISM: Artificial Sequence
<220> FEATURE:
<223> OTHER INFORMATION: MIMAT0002835

<400> SEQUENCE: 52
cucuugaggg aagcacuuuc ugu                                   23

<210> SEQ ID NO 53
<211> LENGTH: 22
<212> TYPE: RNA
<213> ORGANISM: Artificial Sequence
<220> FEATURE:
<223> OTHER INFORMATION: MIMAT0002828

<400> SEQUENCE: 53
uucuccaaaa gggagcacuu uc                                    22

```
<210> SEQ ID NO 54
<211> LENGTH: 22
<212> TYPE: RNA
<213> ORGANISM: Artificial Sequence
<220> FEATURE:
<223> OTHER INFORMATION: MIMAT0005795

<400> SEQUENCE: 54
ucaaaacuga ggggcauuuu cu                                                  22

<210> SEQ ID NO 55
<211> LENGTH: 22
<212> TYPE: RNA
<213> ORGANISM: Artificial Sequence
<220> FEATURE:
<223> OTHER INFORMATION: MIMAT0005451

<400> SEQUENCE: 55
cucuagaggg aagcgcuuuc ug                                                  22

<210> SEQ ID NO 56
<211> LENGTH: 21
<212> TYPE: RNA
<213> ORGANISM: Artificial Sequence
<220> FEATURE:
<223> OTHER INFORMATION: MIMAT0002833

<400> SEQUENCE: 56
cuccagaggg aaguacuuuc u                                                   21

<210> SEQ ID NO 57
<211> LENGTH: 20
<212> TYPE: RNA
<213> ORGANISM: Artificial Sequence
<220> FEATURE:
<223> OTHER INFORMATION: MIMAT0002862

<400> SEQUENCE: 57
cugcaaaggg aagcccuuuc                                                     20

<210> SEQ ID NO 58
<211> LENGTH: 22
<212> TYPE: RNA
<213> ORGANISM: Artificial Sequence
<220> FEATURE:
<223> OTHER INFORMATION: MIMAT0005449

<400> SEQUENCE: 58
cucuagaggg aagcgcuuuc ug                                                  22

<210> SEQ ID NO 59
<211> LENGTH: 22
<212> TYPE: RNA
<213> ORGANISM: Artificial Sequence
<220> FEATURE:
<223> OTHER INFORMATION: MIMAT0005454

<400> SEQUENCE: 59
cucuagaggg aagcgcuuuc ug                                                  22

<210> SEQ ID NO 60
<211> LENGTH: 22
<212> TYPE: RNA
<213> ORGANISM: Artificial Sequence
<220> FEATURE:
<223> OTHER INFORMATION: MIMAT0002831
```

-continued

```
<400> SEQUENCE: 60
cucuagaggg aagcgcuuuc ug                                              22

<210> SEQ ID NO 61
<211> LENGTH: 22
<212> TYPE: RNA
<213> ORGANISM: Artificial Sequence
<220> FEATURE:
<223> OTHER INFORMATION: MIMAT0026609

<400> SEQUENCE: 61
ccucuaaagg gaagcgcuuu cu                                              22

<210> SEQ ID NO 62
<211> LENGTH: 23
<212> TYPE: RNA
<213> ORGANISM: Artificial Sequence
<220> FEATURE:
<223> OTHER INFORMATION: MIMAT0002824

<400> SEQUENCE: 62
uuucaagcca gggggcguuu uuc                                             23

<210> SEQ ID NO 63
<211> LENGTH: 22
<212> TYPE: RNA
<213> ORGANISM: Artificial Sequence
<220> FEATURE:
<223> OTHER INFORMATION: MIMAT0005455

<400> SEQUENCE: 63
cucuagaggg aagcacuuuc ug                                              22

<210> SEQ ID NO 64
<211> LENGTH: 18
<212> TYPE: RNA
<213> ORGANISM: Artificial Sequence
<220> FEATURE:
<223> OTHER INFORMATION: MIMAT0006778

<400> SEQUENCE: 64
ugcuuccuuu cagagggu                                                   18

<210> SEQ ID NO 65
<211> LENGTH: 23
<212> TYPE: RNA
<213> ORGANISM: Artificial Sequence
<220> FEATURE:
<223> OTHER INFORMATION: MIMAT0002848

<400> SEQUENCE: 65
caaagcgcuu cucuuuagag ugu                                             23

<210> SEQ ID NO 66
<211> LENGTH: 22
<212> TYPE: RNA
<213> ORGANISM: Artificial Sequence
<220> FEATURE:
<223> OTHER INFORMATION: MIMAT0002852

<400> SEQUENCE: 66
aucgugcauc ccuuuagagu gu                                              22

<210> SEQ ID NO 67
<211> LENGTH: 22
```

-continued

<212> TYPE: RNA
<213> ORGANISM: Artificial Sequence
<220> FEATURE:
<223> OTHER INFORMATION: MIMAT0002869

<400> SEQUENCE: 67
aaagugcauc cuuuuagagu gu                                              22

<210> SEQ ID NO 68
<211> LENGTH: 22
<212> TYPE: RNA
<213> ORGANISM: Artificial Sequence
<220> FEATURE:
<223> OTHER INFORMATION: MIMAT0002827

<400> SEQUENCE: 68
gagugccuuc uuuuggagcg uu                                              22

<210> SEQ ID NO 69
<211> LENGTH: 18
<212> TYPE: RNA
<213> ORGANISM: Artificial Sequence
<220> FEATURE:
<223> OTHER INFORMATION: MIMAT0002860

<400> SEQUENCE: 69
ugcuuccuuu cagagggu                                                   18

<210> SEQ ID NO 70
<211> LENGTH: 22
<212> TYPE: RNA
<213> ORGANISM: Artificial Sequence
<220> FEATURE:
<223> OTHER INFORMATION: MIMAT0002844

<400> SEQUENCE: 70
caaagcgcuc cccuuuagag gu                                              22

<210> SEQ ID NO 71
<211> LENGTH: 21
<212> TYPE: RNA
<213> ORGANISM: Artificial Sequence
<220> FEATURE:
<223> OTHER INFORMATION: MIMAT0002861

<400> SEQUENCE: 71
aaagcgcuuc ccuucagagu g                                               21

<210> SEQ ID NO 72
<211> LENGTH: 22
<212> TYPE: RNA
<213> ORGANISM: Artificial Sequence
<220> FEATURE:
<223> OTHER INFORMATION: MIMAT0002863

<400> SEQUENCE: 72
gaaagcgcuu cccuuugcug ga                                              22

<210> SEQ ID NO 73
<211> LENGTH: 22
<212> TYPE: RNA
<213> ORGANISM: Artificial Sequence
<220> FEATURE:
<223> OTHER INFORMATION: MIMAT0002827

<400> SEQUENCE: 73

```
gagugccuuc uuuuggagcg uu                                              22

<210> SEQ ID NO 74
<211> LENGTH: 22
<212> TYPE: RNA
<213> ORGANISM: Artificial Sequence
<220> FEATURE:
<223> OTHER INFORMATION: MIMAT0002823

<400> SEQUENCE: 74
aagugcuguc auagcugagg uc                                              22

<210> SEQ ID NO 75
<211> LENGTH: 21
<212> TYPE: RNA
<213> ORGANISM: Artificial Sequence
<220> FEATURE:
<223> OTHER INFORMATION: MIMAT0002842

<400> SEQUENCE: 75
gaaagcgcuu cucuuuagag g                                               21

<210> SEQ ID NO 76
<211> LENGTH: 22
<212> TYPE: RNA
<213> ORGANISM: Artificial Sequence
<220> FEATURE:
<223> OTHER INFORMATION: MIMAT0002853

<400> SEQUENCE: 76
caaagugccu cccuuuagag ug                                              22

<210> SEQ ID NO 77
<211> LENGTH: 22
<212> TYPE: RNA
<213> ORGANISM: Artificial Sequence
<220> FEATURE:
<223> OTHER INFORMATION: MIMAT0002857

<400> SEQUENCE: 77
aucgugcauc ccuuuagagu gu                                              22

<210> SEQ ID NO 78
<211> LENGTH: 22
<212> TYPE: RNA
<213> ORGANISM: Artificial Sequence
<220> FEATURE:
<223> OTHER INFORMATION: MIMAT0002854

<400> SEQUENCE: 78
aacgcacuuc ccuuuagagu gu                                              22

<210> SEQ ID NO 79
<211> LENGTH: 21
<212> TYPE: RNA
<213> ORGANISM: Artificial Sequence
<220> FEATURE:
<223> OTHER INFORMATION: MIMAT0002850

<400> SEQUENCE: 79
gaaggcgcuu cccuuuggag u                                               21

<210> SEQ ID NO 80
<211> LENGTH: 24
<212> TYPE: RNA
<213> ORGANISM: Artificial Sequence
```

```
<220> FEATURE:
<223> OTHER INFORMATION: MIMAT0002858

<400> SEQUENCE: 80
acaaagugcu ucccuuuaga gugu                                          24

<210> SEQ ID NO 81
<211> LENGTH: 22
<212> TYPE: RNA
<213> ORGANISM: Artificial Sequence
<220> FEATURE:
<223> OTHER INFORMATION: MIMAT0002839

<400> SEQUENCE: 81
gaaggcgcuu cccuuuagag cg                                            22

<210> SEQ ID NO 82
<211> LENGTH: 22
<212> TYPE: RNA
<213> ORGANISM: Artificial Sequence
<220> FEATURE:
<223> OTHER INFORMATION: MIMAT0002856

<400> SEQUENCE: 82
aaagugcuuc ucuuuggugg gu                                            22

<210> SEQ ID NO 83
<211> LENGTH: 22
<212> TYPE: RNA
<213> ORGANISM: Artificial Sequence
<220> FEATURE:
<223> OTHER INFORMATION: MIMAT0002836

<400> SEQUENCE: 83
gaaagugcuu ccuuuuagag gc                                            22

<210> SEQ ID NO 84
<211> LENGTH: 22
<212> TYPE: RNA
<213> ORGANISM: Artificial Sequence
<220> FEATURE:
<223> OTHER INFORMATION: MIMAT0002829

<400> SEQUENCE: 84
aagugccucc uuuuagagug uu                                            22

<210> SEQ ID NO 85
<211> LENGTH: 22
<212> TYPE: RNA
<213> ORGANISM: Artificial Sequence
<220> FEATURE:
<223> OTHER INFORMATION: MIMAT0002868

<400> SEQUENCE: 85
aaaaugguuc ccuuuagagu gu                                            22

<210> SEQ ID NO 86
<211> LENGTH: 22
<212> TYPE: RNA
<213> ORGANISM: Artificial Sequence
<220> FEATURE:
<223> OTHER INFORMATION: MIMAT0002869

<400> SEQUENCE: 86
aaagugcauc cuuuuagagu gu                                            22
```

```
<210> SEQ ID NO 87
<211> LENGTH: 22
<212> TYPE: RNA
<213> ORGANISM: Artificial Sequence
<220> FEATURE:
<223> OTHER INFORMATION: MIMAT0002834

<400> SEQUENCE: 87
aaagugcuuc ccuuuggacu gu                                              22

<210> SEQ ID NO 88
<211> LENGTH: 23
<212> TYPE: RNA
<213> ORGANISM: Artificial Sequence
<220> FEATURE:
<223> OTHER INFORMATION: MIMAT0002840

<400> SEQUENCE: 88
gaacgcgcuu cccauagag ggu                                              23

<210> SEQ ID NO 89
<211> LENGTH: 22
<212> TYPE: RNA
<213> ORGANISM: Artificial Sequence
<220> FEATURE:
<223> OTHER INFORMATION: MIMAT0002867

<400> SEQUENCE: 89
acaaagugcu ucccuuuaga gu                                              22

<210> SEQ ID NO 90
<211> LENGTH: 22
<212> TYPE: RNA
<213> ORGANISM: Artificial Sequence
<220> FEATURE:
<223> OTHER INFORMATION: MIMAT0002837

<400> SEQUENCE: 90
aaagugcauc cuuuuagagg uu                                              22

<210> SEQ ID NO 91
<211> LENGTH: 21
<212> TYPE: RNA
<213> ORGANISM: Artificial Sequence
<220> FEATURE:
<223> OTHER INFORMATION: MIMAT0002843

<400> SEQUENCE: 91
aaagugcuuc cuuuuagagg g                                               21

<210> SEQ ID NO 92
<211> LENGTH: 22
<212> TYPE: RNA
<213> ORGANISM: Artificial Sequence
<220> FEATURE:
<223> OTHER INFORMATION: MIMAT0002832

<400> SEQUENCE: 92
aaagugcauc uuuuuagagg au                                              22

<210> SEQ ID NO 93
<211> LENGTH: 22
<212> TYPE: RNA
<213> ORGANISM: Artificial Sequence
<220> FEATURE:
<223> OTHER INFORMATION: MIMAT0002830
```

<400> SEQUENCE: 93
aagugcuucc uuuuagaggg uu                                          22

<210> SEQ ID NO 94
<211> LENGTH: 22
<212> TYPE: RNA
<213> ORGANISM: Artificial Sequence
<220> FEATURE:
<223> OTHER INFORMATION: MIMAT0002846

<400> SEQUENCE: 94
aaagugcuuc cuuuuagagg gu                                          22

<210> SEQ ID NO 95
<211> LENGTH: 1165
<212> TYPE: DNA
<213> ORGANISM: Artificial Sequence
<220> FEATURE:
<223> OTHER INFORMATION: upstream promoter region of the C19MC miRNA

<400> SEQUENCE: 95

```
cgccgcggcc tcctccctct accataccc aatgccaggc tcacttcctg ccgcctgcct      60
ggaacgggc tgctcatgca tcccccacgc cctctgaagc cccccggcg cactccacgc      120
cctctcgcct gacccctgtt tccgctgccg gcgtctccac acccctgac gccgccacgc     180
cctggaccga ggtctctaga gctgcgcgcc ggctgcacgt cccttaggag tttccgtgcg    240
ccacgaggcg ctggcgcgcg tctcccggcc catccacccc gggcccggcg acaccttctc    300
ttgccacctg gaaccaacat cttggttccc ttttgaggga tcagaacttg tttaattgga    360
atacggcaaa attctgaatt tttctgccgt ctctattcca acttcagagt tctgccgtcc    420
agccctgcga caatcttccg gtgccaacgc ggcaggtcag tatgtatccc ccacgatgcc    480
cccccgggcca cgggccccta gttaacaggt ttcccttcg cccgctgcct ggaagtatcg    540
ccacctcgcc ccgcccaacc ccccaccaga cagctctgca gccacagccc ctcatccaac    600
caggaagtcc agggcccatc tggcccgcta gacctcggga aaccacgcg tcagagcacc    660
cattaagagg ggtccaggcc gggcgcggtg gttcgcatca gggcgccat taagaggggt     720
ccaggctggg cacggtggtt cccatcaggg cgcccattaa gagggtcca ggccgggcgc     780
ggtggttcgc atcagggcgc ccattaagag gggtccaggc tgggcacggt ggttcccatc    840
agggcgccca ttaagagggg tccaggctgg gcacggtggt tcccatcagg gcacccatta    900
agagggtcc aggccgggcg cggtcgttcg cattagagca cccattaaga ggggtccagg    960
ctgggcacgg tggttcccat cagggcgccc attaagaggg gtccaggccg ggcgcggtgg  1020
ttcgcatcag ggcgcccatt aagaggggtc caggctgggc acggtggttc ccatcagggc  1080
gcccattaag aggggtccag gctgggcacg gtggttccca tcagggcacc cattaagagg  1140
ggtccaggcc gggcgcggtc gttcg                                        1165
```

<210> SEQ ID NO 96
<211> LENGTH: 25
<212> TYPE: DNA
<213> ORGANISM: Artificial Sequence
<220> FEATURE:
<223> OTHER INFORMATION: gRNA #759

<400> SEQUENCE: 96
caccgcaaat cctaggcctg ccctg                                        25

```
<210> SEQ ID NO 97
<211> LENGTH: 25
<212> TYPE: DNA
<213> ORGANISM: Artificial Sequence
<220> FEATURE:
<223> OTHER INFORMATION: gRNA #620

<400> SEQUENCE: 97
caccggtgag ctgatgatcg ctcca                                              25
```

METHODS OF MEASURING C19MC MIRNA IN A POST-NATAL TISSUE AND USES THEREOF

CROSS-REFERENCE TO RELATED APPLICATIONS

This application claims the benefit of and priority to U.S. Provisional Patent Application No. 62/350,232, filed on Jun. 15, 2016, entitled "METHODS OF MEASURING C19MC miRNA IN A POST-NATAL TISSUE AND USES THEREOF," the contents of which is incorporated by reference herein in its entirety.

STATEMENT REGARDING FEDERALLY SPONSORED RESEARCH OR DEVELOPMENT

This invention was made with government support under grant number 1R01HL128411-01 awarded by the National Institutes of Health. The government has certain rights in the invention.

SEQUENCE LISTING

This application contains a sequence listing filed in electronic form as an ASCII.txt file entitled 292105-1340.K created on Jun. 12, 2017. The content of the sequence listing is incorporated herein in its entirety.

BACKGROUND

Infantile hemangiomas (IH) are common benign tumors in childhood, diagnosed in approximately 10% of children aged <1 year, with increased incidence in premature infants and females (Haggstrom, et al., *J. Pediatr.* 150, 291-294, 2007; Ritter, et al., *Expert Rev Mol Med.* 9:32, 1-19, 2007). Initial stages of IH characterized by rapid proliferation followed by a regressive involuting phase that leaves a fibro fatty residuum (Itinteang, et al., *J. Clin. Pathol.* 64, 870-874, 2011). Majority of IH lesions do not require medical intervention. However, life threatening lesions or lesions that negatively affect vision, hearing, or breathing require treatment. Current treatments include systemic steroids, immune regulators, Interferon alpha, propranolol, radiation, laser treatment, and surgery, all of which have some potential negative side effects (Léauté-Labrèze, et al., *N. Engl. J. Med.*, vol. 372, no. 8, pp. 735-746, 2015). Vasculogenesis, vessel regression and the underlying mechanisms involved in the post-natal IH remain elusive.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
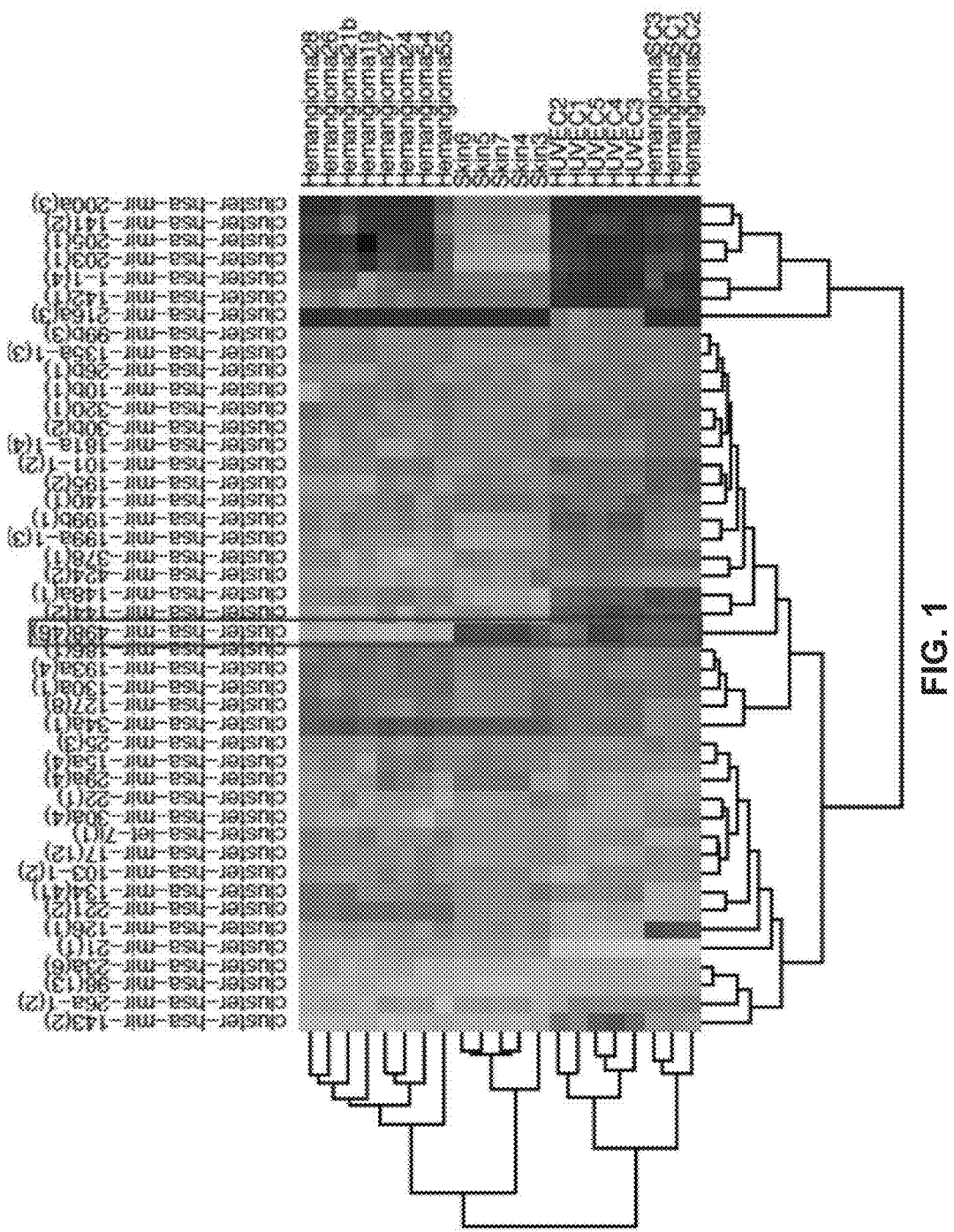
FIG. 1 shows results from a hierarchical clustering that was performed by analyzing the differential global microRNA expression in eight Hemangioma samples compared with 5 samples of normal skin, 5 samples of HUVECs and three samples of HemSC. The heatmap shown in FIG. 1 demonstrates the average change in expression of each miRNA cluster. Graded colors are proportional to expression levels expressed as Log 2 read frequency (yellow (light gray) high, blue (dark gray) low, and black absent).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "seed sequence" or "seed region" can refer to a 7 nucleotide long region within a microRNA that can be conserved between 2 or more microRNAs that is typically located from nucleotides 2-7 from the 5' end of the mature microRNA.

As used herein, "about," "approximately," and the like, when used in connection with a numerical variable, generally refers to the value of the variable and to all values of the variable that are within the experimental error (e.g., within the 95% confidence interval for the mean) or within +−10% of the indicated value, whichever is greater.

As used herein, "control" is an alternative subject or sample used in an experiment for comparison purpose and included to minimize or distinguish the effect of variables other than an independent variable.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "preventative" refers to hindering or stopping a disease or condition before it occurs or while the disease or condition is still in the sub-clinical phase.

As used herein, "therapeutic" can refer to treating or curing a disease or condition.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like. The terms "guide polynucleotide," "guide sequence," or "guide RNA" as used herein refers to any polynucleotide sequence having sufficient complementarity with a target polynucleotide sequence to hybridize with the target sequence and direct sequence-specific binding of a CRISPR complex to the target sequence. The degree of complementarity between a guide polynucleotide and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). A guide polynucleotide (also referred to herein as a guide sequence and includes single guide sequences (sgRNA)) can be about or more than about 5, 10, 11, 12, 13, 14, 15, 16, 17, 18, 19, 20, 21, 22, 23, 24, 25, 26, 27, 28, 29, 30, 35, 40, 45, 50, 75, 90, 100, 110, 112, 115, 120, 130, 140, or more nucleotides in length. The guide polynucleotide can include a nucleotide sequence that is complementary to a target DNA sequence. This portion of the guide sequence can be referred to as the complementary region of the guide RNA. In some contexts, the two are distinguished from one another by calling one the complementary region or target region and the rest of the polynucleotide the guide sequence or tracrRNA. The guide sequence can also include one or more miRNA target sequences coupled to the 3' end of the guide sequence. The guide sequence can include one or more MS2 RNA aptamers incorporated within the portion of the guide strand that is not the complementary portion. As used herein the term guide sequence can include any specially modified guide sequences, including but not limited to those configured for use in synergistic activation mediator (SAM) implemented CRISPR (*Nature* 517, 583-588 (29 Jan. 2015) or suppression (Cell Volume 154, Issue 2, 18 Jul. 2013, Pages 442-451). A guide polynucleotide can be less than about 150, 125, 75, 50, 45, 40, 35, 30, 25, 20, 15, 12, or fewer nucleotides in length. The ability of a guide polynucleotide to direct sequence-specific binding of a CRISPR complex to a target sequence may be assessed by any suitable assay. For example, the components of a CRISPR system sufficient to form a CRISPR complex, including the guide polynucleotide to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide polynucleotide to be tested and a control guide polynucleotide different from the test guide polynucleotide, and comparing binding or rate of cleavage at the target sequence between the test and control guide polynucleotide reactions. Other assays are possible, and will occur to those skilled in the art.

A complementary region of the gRNA can be configured to target any DNA region of interest. The complementary region of the gRNA and the gRNA can be designed using a suitable gRNA design tool. Suitable tools are known in the art and are available to the skilled artisan. As such, the constructs described herein are enabled for any desired target DNA so long as it is CRISPR compatible according to the known requirements for CRISPR activation.

A guide polynucleotide can be selected to reduce the degree of secondary structure within the guide polynucleotide. Secondary structure may be determined by any suitable polynucleotide folding algorithm. Some programs are based on calculating the minimal Gibbs free energy. An example of one such algorithm is mFold, as described by Zuker & Stiegler ((1981) *Nucleic Acids Res.* 9, 133-148). Another example folding algorithm is the online webserver RNAfold, developed at Institute for Theoretical Chemistry at the University of Vienna, using the centroid structure prediction algorithm (see e.g. Gruber et al., (2008) *Cell* 106: 23-24; and Carr & Church (2009) *Nature Biotechnol.* 27: 1151-1162).

Homology-directed repair (HDR) refers to a mechanism in cells to repair double-stranded and single stranded DNA breaks. Homology-directed repair includes homologous recombination (HR) and single-strand annealing (SSA) (Lieber. (2010) *Annu. Rev. Biochem.* 79: 181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks.

Error-prone DNA repair refers to mechanisms that can produce mutations at double-strand break sites. The Non-Homologous-End-Joining (NHEJ) pathways are the most common repair mechanism to bring the broken ends together (Bleuyard et al., (2006) *DNA Repair* 5: 1-12). The structural integrity of chromosomes is typically preserved by the repair, but deletions, insertions, or other rearrangements are possible. The two ends of one double-strand break are the most prevalent substrates of NHEJ (Kirik et al., (2000) *EMBO J.* 19: 5562-5566), however if two different double-strand breaks occur, the free ends from different breaks can be ligated and result in chromosomal deletions (Siebert & Puchta, (2002) *Plant Cell* 14:1121-1131), or chromosomal translocations between different chromosomes (Pacher et al., (2007) *Genetics* 175: 21-29).

It will also be appreciated that CRISPR can also be used to activate specific genes through CRISPR/synergistic activation mediator procedures. These procedures can utilize a guide polynucleotide that incorporates 2 MS2 RNA aptamers at the tetraloop and the stem-loop of the guide RNA such as that described in, but not limited to (*Nature* 517, 583-588 (29 Jan. 2015).

As used herein, "specific binding" refers to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" can refer to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic RNA molecule including but not limited to tRNA, siRNA, piRNA, miRNA, long-non-coding RNA and shRNA.

As used herein, "deoxyribonucleic acid (DNA)" and "ribonucleic acid (RNA)" generally refer to any polyribonucleotide or polydeoxyribonucleotide, which can be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "nucleic acid sequence" and "oligonucleotide" also encompasses a nucleic acid and polynucleotide as defined elsewhere herein.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" can refer to a small non-coding RNA molecule containing about 21 to about 23 nucleotides found in organisms, which functions in transcriptional and post-transcriptional regulation of transcription and translation of RNA. "MicroRNA" can exist as part of a larger nucleic acid molecule such as a stem-loop structure that can be processed by a cell and yield a microRNA of about 21-23 nucleotides.

As used herein, "pharmaceutically acceptable carrier, diluent, binders, lubricants, glidant, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "overexpressed" or "overexpression" refers to an increased expression level of an RNA (coding or non-coding RNA) or protein product encoded by a gene as compared to the level of expression of the RNA or protein product in a normal or control cell.

As used herein, "underexpressed" or "underexpression" refers to decreased expression level of an RNA (coding or non-coding RNA) or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein with reference to the relationship between DNA, cDNA, cRNA, RNA, and protein/peptides, "corresponding to" can refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "promoter" can include all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, "identity," ca refer to a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides of the present disclosure.

As used herein "miRNA target" or "miRNA target sequence" can refer to the nucleic acid sequence, typically RNA, that a miRNA specifically binds to. The miRNA target can be or include a sequence that is complementary to the miRNA. As an example, microRNA 126 (miR-126) can specifically bind a miR-126 target. Binding of a miRNA to a miRNA target can result in transcription and/or translation inhibition of the nucleic acid sequence, such as through degradation of the nucleic acid sequence (typically mRNA or other type of RNA), that the miRNA target is part of). A micro RNA does not have to have perfect complementarity to a miRNA target for specific binding or transcription inhibition to occur.

Discussion

Infantile hemangiomas (IH) are benign vascular tumors of childhood characterized by EC proliferation. IH lesions generally follow the same pattern. They appear during the first 4-6 weeks of life with rapid growth up to 6 months of age followed by slow spontaneous involution phase over a period of 3-7 years that often leaves behind a fibro fatty layer (Ritter, et al., *Expert Rev Mol Med.* 9:32, 1-19, 2007; Calicchio, et al., *Am. J. Pathol.* 174:5, 1638-1649, 2009);

Itinteang, et al., *J. Clin. Pathol.* 64, 870-874, 2011). IH affects up to 10% of newborns with about 60% localized in the head and neck region (Schultz, et al., *PLoS One* 10:10, e0113168, 2015). It is prevalent among Caucasian female infants who are more likely to have been born premature and be products of multiple pregnancies (Haggstrom, et al., *J. Pediatr.* 150, 291-294, 2007). The Haggstrom et. al. study reports a link between IH and higher maternal age, preeclampsia and placenta previa (Haggstrom, et al., *J. Pediatr.* 150, 291-294, 2007). IH has also been associated with placental trauma caused by chorionic villous sampling during pregnancy and other placental disruptions (North, et al., *Arch. Dermatol.* 137, 559-570, May 2001; López Gutiérrez, et al., *Pediatr. Dermatol.* 24:4, 353-355, 2007). Despite the prevalence of these tumors, the pathogenesis has not yet been elucidated.

Although most IH are not worrisome, around 12% of IH are significantly complex with life threatening lesions and therefore require treatment. Historically, systemic glucocorticoids, interferon alpha and vincristine have been used in the treatment of IH (Léauté-Labrèze, *N. Engl. J. Med., vol.* 372, no. 8, pp. 735-746, 2015). These treatments have varying efficacies and are not without their side effects (Leaute-Labreze, *N. Engl. J. Med., vol.* 372, no. 8, pp. 735-746, 2015). Propranolol was serendipitously discovered to cause early involution of IH tumors when it was used to treat children with IH who had developed obstructive hypertrophic cardiomyopathy (Léauté-Labrèze, *New Engl. J. Med.* 358: 24, 2649-51, 2008). The mechanism by which propranolol causes the switch from proliferating phase to involuting phase is not yet known. Various explanations have been proposed, including vasoconstriction, decreased expression of vascular endothelial growth factor (VEGF) and beta fibroblast growth factor genes, apoptosis of capillary endothelial cells, blockage of the G protein-coupled receptor kinases Leu41 (Storch, et al., *Br. J. Dermatol.* 163:2, 269-274, 2010; Mansouri, et al., *Journal of Skin and Stem Cell* 1:2, 1-5, 2014). Propranolol is the current drug of choice with some adverse events such as hypoglycemia, hypotension and bradycardia (Storch, et al., *Br. J. Dermatol.* 163:2, 269-274, 2010). There is therefore a need for the development of a safer targeted therapies based on a deeper understanding of the pathogenesis of IH.

With that said, described herein are methods of measuring expression of microRNA(s), including but not limited to those of the chromosome 19 miRNA cluster (C19MC), in a tissue and/or bodily fluid. Also described herein are methods including the step of measuring methylation of the C19MC promoter region in a tissue and/or bodily fluid. Also provided herein are methods of treating IH and other diseases or disorders mediated by C19MC microRNA by administering to a subject a compound that can modulate the expression of C19MC microRNA to a subject in need thereof.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays for Measuring C19MC microRNA

MicroRNAs (miRNA) can play important roles in vascular biology (Small, et al., *Nature* 469:7330, 336-342, 2011). The role of miRNAs in the onset and progression of IH has never been investigated. Data shown in the Examples demonstrate results of small RNAsequencing analysis of IH specimen shows significant upregulation of the chromosome 19 miRNA cluster (C19MC). C19MC contains 46 intronic miRNA genes that span over 100 kb of genomic DNA on chromosome 19 (Noguer-Dance, *Hum. Mol. Genet.* 19:18, 3566-3582, 2010; Mouillet, et al., *Am. J. Obstet. Gynecol.* 213:4, S163-S172, 2015). This cluster produces 58 mature miRNA species that are expressed only in the placenta and have no orthologous regions in the mouse genome (Mouillet, et al., *Am. J. Obstet. Gynecol.* 213:4, S163-S172, 2015). Recent studies implicate C19MC miRNAs in cellular processes such as proliferation, invasion and differentiation (Mouillet, et al., *Am. J. Obstet. Gynecol.* 213:4, S163-S172, 2015). C19MC is regulated by genomic imprinting with only the paternal allele expressed in the placenta (Noguer-Dance, *Hum. Mol. Genet.* 19:18, 3566-3582, 2010). Its expression is controlled by DNA methylation of an upstream CpG rich promoter region (Noguer-Dance, *Hum. Mol. Genet.* 19:18, 3566-3582, 2010). C19MC miRNAs in the pre-natal placenta are involved in regulation of cell proliferation, invasion, and differentiation.

Provided herein are assays that can determine the expression and/or CpG methylation of the upstream C19MC promoter region in post-natal tissue. Insofar as C19MC miRNAs and/or are not routinely examined, if at all, in post-natal tissues, the assays and methods provided herein are not routine in the art.

The methods can include the steps of obtaining a post-natal tissue or bodily fluid sample from a subject and measuring the expression or presence, either quantitatively or qualitatively, of at least one or more C19MC miRNAs. In embodiments, the expression or presence, either quantitatively or qualitatively, or one or more control miRNAs can also be measured. C19MC miRNAs that can be measured can be one or more of the following miRNAs shown in Table 1.

TABLE 1

| miRNA | miRBase Accession No./ Precursor Sequence (stem-loop) (5'-3') | SEQ ID NO: | miRBase Accession No./ 5p Mature Sequence ID and Sequence | SEQ ID NO: | miRBase Accession No./ 3p Mature Sequence ID and Sequence | SEQ ID NO: |
|---|---|---|---|---|---|---|
| miR-516a | MI0003180 UCUCAGGCUGUGACCUUC UCGAGGAAAGAAGCACUU UCUGUUGUCUGAAAGAAA AGAAAGUGCUUCCUUUCA GAGGGUUACGGUUUGAGA | 1 | MIMAT0004770 UUCUCGA GGAAAGA AGCACUU UC | 36 | MIMAT0006778 UGCUUCCU UUCAGAGG GU | 64 |

TABLE 1-continued

| miRNA | miRBase Accession No./ Precursor Sequence (stem-loop) (5'-3') | SEQ ID NO: | miRBase Accession No./ 5p Mature Sequence ID and Sequence | SEQ ID NO: | miRBase Accession No./ 3p Mature Sequence ID and Sequence | SEQ ID NO: |
|---|---|---|---|---|---|---|
| miR-518c | MI0003159 GCGAGAAGAUCUCAUGCU GUGACUCUCUGGAGGGAA GCACUUUCUGUUGUCUGA AAGAAAACAAAGCGCUUC UCUUUAGAGUGUUACGGU UUGAGAAAAGC | 2 | MIMAT0002847 UCUCUGG AGGGAAG CACUUUC UG | 37 | MIMAT0002848 CAAAGCGC UUCUCUUU AGAGUGU | 65 |
| miR-517a | MI0003161 UCUCAGGCAGUGACCCUC UAGAUGGAAGCACUGUCU GUUGUAUAAAGAAAAGA UCGUGCAUCCCUUUAGAG UGUUACUGUUUGAGA | 3 | MIMAT0002851 CCUCUAG AUGGAAG CACUGUC U | 38 | MIMAT0002852 AUCGUGCA UCCCUUUA GAGUGU | 66 |
| miR-519a-1 | MI0003178 CUCAGGCUGUGACACUCU AGAGGGAAGCGCUUUCUG UUGUCUGAAAGAAAGGAA AGUGCAUCCUUUUAGAGU GUUACUGUUUGAG | 4 | MIMAT0005452 CUCUAGA GGGAAGC GCUUUCU G | 39 | MIMAT0002869 AAAGUGCA UCCUUUUA GAGUGU | 67 |
| miR-515-1 | MI0003144 UCUCAUGCAGUCAUUCUC CAAAAGAAAGCACUUUCU GUUGUCUGAAAGCAGAGU GCCUUCUUUUGGAGCGUU ACUGUUUGAGA | 5 | MIMAT0002826 UUCUCCA AAAGAAAG CACUUUC UG | 40 | MIMAT0002827 GAGUGCCU UCUUUUGG AGCGUU | 68 |
| miR-516b-1 | MI0003172 UCUCAGGCUGUGACCAUC UGGAGGUAAGAAGCACUU UCUGUUUUGUGAAAGAAA AGAAAGUGCUUCCUUUCA GAGGGUUACUCUUUGAGA | 6 | MIMAT0002859 AUCUGGA GGUAAGA AGCACUU U | 41 | MIMAT0002860 UGCUUCCU UUCAGAGG GU | 69 |
| miR-518b | MI0003156 UCAUGCUGUGGCCCUCCA GAGGGAAGCGCUUUCUGU UGUCUGAAAGAAAACAAA GCGCUCCCCUUUAGAGGU UUACGGUUUGA | 7 | — | | MIMAT0002844 CAAAGCGC UCCCCUUU AGAGGU | 70 |
| miR-518e | MI0003169 UCUCAGGCUGUGACCCUC UAGAGGGAAGCGCUUUCU GUUGGCUAAAAGAAAGA AAGCGCUUCCCUUCAGAG UGUUAACGCUUUGAGA | 8 | MIMAT0005450 CUCUAGA GGGAAGC GCUUUCU G | 42 | MIMAT0002861 AAAGCGCU UCCCUUCA GAGUG | 71 |
| miR-518a-1 | MI0003170 UCUCAAGCUGUGACUGCA AAGGGAAGCCCUUUCUGU UGUCUGAAAGAAGAGAAA GCGCUUCCCUUUGCUGGA UUACGGUUUGAGA | 9 | MIMAT0005457 CUGCAAA GGGAAGC CCUUUC | 43 | MIMAT0002863 GAAAGCGC UUCCCUUU GCUGGA | 72 |
| miR-515-2 | MI0003147 UCUCAUGCAGUCAUUCUC CAAAAGAAAGCACUUUCU GUUGUCUGAAAGCAGAGU GCCUUCUUUUGGAGCGUU ACUGUUUGAGA | 10 | MIMAT0002826 UUCUCCA AAAGAAAG CACUUUC UG | 44 | MIMAT0002827 GAGUGCCU UCUUUUGG AGCGUU | 73 |
| miR-512-1 | MI0003140 UCUCAGUCUGUGGCACUC AGCCUUGAGGGCACUUUC UGGUGCCAGAAUGAAAGU GCUGUCAUAGCUGAGGUC CAAUGACUGAGG | 11 | MIMAT0002822 CACUCAG CCUUGAG GGCACUU UC | 45 | MIMAT0002823 AAGUGCUG UCAUAGCU GAGGUC | 74 |
| miR- | MI0003154 | 12 | MIMAT0002841 | 46 | MIMAT0002842 | 75 |

TABLE 1-continued

| miRNA | miRBase Accession No./ Precursor Sequence (stem-loop) (5'-3') | SEQ ID NO: | miRBase Accession No./ 5p Mature Sequence ID and Sequence | SEQ ID NO: | miRBase Accession No./ 3p Mature Sequence ID and Sequence | SEQ ID NO: |
|---|---|---|---|---|---|---|
| 518f | UCUCAUGCUGUGACCCUC UAGAGGGAAGCACUUUCU CUUGUCUAAAAGAAAAGA AAGCGCUUCUCUUUAGAG GAUUACUCUUUGAGA | | CUCUAGA GGGAAGC ACUUUCU C | | GAAAGCGC UUCUCUUU AGAGG | |
| miR-1283-1 | MI0003832 CUCAAGCUAUGAGUCUAC AAAGGAAAGCGCUUUCUG UUGUCAGAAAGAAGAGAA AGCGCUUCCCUUUUGAGG GUUACGGUUUGAGAA | 13 | MIMAT0005799 UCUACAAA GGAAAGC GCUUUCU | 47 | — | |
| miR-519d | MI0003162 UCCCAUGCUGUGACCCUC CAAAGGGAAGCGCUUUCU GUUUGUUUUCUCUUAAAC AAAGUGCCUCCCUUUAGA GUGUUACCGUUUGGGA | 14 | — | | MIMAT0002853 CAAAGUGC CUCCCUUU AGAGUG | 76 |
| miR-517b | MI0003165 GUGACCCUCUAGAUGGAA GCACUGUCUGUUGUCUAA GAAAAGAUCGUGCAUCCC UUUAGAGUGUUAC | 15 | MIMAT0002851 CCUCUAG AUGGAAG CACUGUC U | 48 | MIMAT0002857 AUCGUGCA UCCCUUUA GAGUGU | 77 |
| miR-521-2 | MI0003163 UCUCGGGCUGUGACUCUC CAAAGGGAAGAAUUUCU CUUGUCUAAAAGAAAAGA ACGCACUUCCCUUUAGAG UGUUACCGUGUGAGA | 16 | — | | MIMAT0002854 AACGCACU UCCCUUUA GAGUGU | 78 |
| miR-524 | MI0003160 UCUCAUGCUGUGACCCUA CAAAGGGAAGCACUUUCU CUUGUCCAAAGGAAAAGA AGGCGCUUCCCUUUGGAG UGUUACGGUUUGAGA | 17 | MIMAT0002849 CUACAAA GGGAAGC ACUUUCU C | 49 | MIMAT0002850 GAAGGCGC UUCCCUUU GGAGU | 79 |
| miR-520g | MI0003166 UCCCAUGCUGUGACCCUC UAGAGGAAGCACUUUCUG UUUGUUGUCUGAGAAAAA ACAAAGUGCUUCCCUUUA GAGUGUUACCGUUUGGGA | 18 | — | | MIMAT0002858 ACAAAGUG CUUCCCUU UAGAGUGU | 80 |
| miR-525 | MI0003152 CUCAAGCUGUGACUCUCC AGAGGGAUGCACUUUCUC UUAUGUGAAAAAAAGAA GGCGCUUCCCUUUAGAGC GUUACGGUUUGGG | 19 | MIMAT0002838 CUCCAGA GGGAUGC ACUUUCU | 50 | MIMAT0002839 GAAGGCGC UUCCCUUU AGAGCG | 81 |
| miR-520d | MI0003164 UCUCAAGCUGUGAGUCUA CAAAGGGAAGCCCUUUCU GUUGUCUAAAAGAAAAGA AAGUGCUUCUCUUUGGUG GGUUACGGUUUGAGA | 20 | MIMAT0002855 CUACAAA GGGAAGC CCUUUC | 51 | MIMAT0002856 AAAGUGCU UCUCUUUG UGGGU | 82 |
| miR-526b | MI0003150 UCAGGCUGUGACCCUCUU GAGGGAAGCACUUUCUGU UGUCUGAAAGAAGAGAAA GUGCUUCCUUUUAGAGGC UUACUGUCUGA | 21 | MIMAT0002835 CUCUUGA GGGAAGC ACUUUCU GU | 52 | MIMAT0002836 GAAAGUGC UUCCUUUU AGAGGC | 83 |
| miR-519e | MI0003145 UCUCAUGCAGUCAUUCUC CAAAGGGAGCACUUUCU GUUUGAAAGAAAACAAAG | 22 | MIMAT0002828 UUCUCCA AAGGGA GCACUUU | 53 | MIMAT0002829 AAGUGCCU CCUUUUAG AGUGUU | 84 |

TABLE 1-continued

| miRNA | miRBase Accession No./ Precursor Sequence (stem-loop) (5'-3') | SEQ ID NO: | miRBase Accession No./ 5p Mature Sequence ID and Sequence | SEQ ID NO: | miRBase Accession No./ 3p Mature Sequence ID and Sequence | SEQ ID NO: |
|---|---|---|---|---|---|---|
| | UGCCUCCUUUUAGAGUGU UACUGUUUGAGA | | C | | | |
| miR-1323 | MI0003786 ACUGAGGUCCUCAAAACU GAGGGGCAUUUUCUGUGG UUUGAAAGGAAAGUGCAC CCAGUUUUGGGGAUGUCA A | 23 | MIMAT0005795 UCAAAACU GAGGGGC AUUUUCU | 54 | — | |
| miR-522 | MI0003177 UCUCAGGCUGUGUCCCUC UAGAGGGAAGCGCUUUCU GUUGUCUGAAAGAAAGA AAAUGGUUCCCUUUAGAG UGUUACGCUUUGAGA | 24 | MIMAT0005451 CUCUAGA GGGAAGC GCUUUCU G | 55 | MIMAT0002868 AAAAUGGU UCCCUUUA GAGUGU | 85 |
| miR-519a-2 | MI0003182 UCUCAGGCUGUGUCCCUC UACAGGGAAGCGCUUUCU GUUGUCUGAAAGAAAGGA AAGUGCAUCCUUUUAGAG UGUUACUGUUUGAGA | 25 | — | | MIMAT0002869 AAAGUGCA UCCUUUUA GAGUGU | 86 |
| miR-520a | MI0003149 CUCAGGCUGUGACCCUCC AGAGGGAAGUACUUUCUG UUGUCUGAGAGAAAGAA AGUGCUUCCCUUUGGACU GUUUCGGUUUGAG | 26 | MIMAT0002833 CUCCAGA GGGAAGU ACUUUCU | 56 | MIMAT0002834 AAAGUGCU UCCCUUUG GACUGU | 87 |
| miR-527 | MI0003179 UCUCAAGCUGUGACUGCA AAGGGAAGCCCUUUCUGU UGUCUAAAAGAAAAGAAA GUGCUUCCCUUUGGUGAA UUACGGUUUGAGA | 27 | MIMAT0002862 CUGCAAA GGGAAGC CCUUUC | 57 | — | |
| miR-523 | MI0003153 UCUCAUGCUGUGACCCUC UAGAGGGAAGCGCUUUCU GUUGUCUGAAAGAAAGA ACGCGCUUCCCUAUAGAG GGUUACCCUUUGAGA | 28 | MIMAT0005449 CUCUAGA GGGAAGC GCUUUCU G | 58 | MIMAT0002840 GAACGCGC UUCCCUAU AGAGGGU | 88 |
| miR-520h | MI0003175 UCCCAUGCUGUGACCCUC UAGAGGAAGCACUUUCUG UUUGUUGUCUGAGAAAAA ACAAAGUGCUUCCCUUUA GAGUUACUGUUUGGGA | 29 | — | | MIMAT0002867 ACAAAGUG CUUCCCUU UAGAGU | 89 |
| miR-519b | MI0003151 CAUGCUGUGACCCUCUAG AGGGAAGCGCUUUCUGUU GUCUGAAAGAAAAGAAAG UGCAUCCUUUUAGAGGUU ACUGUUUG | 30 | MIMAT0005454 CUCUAGA GGGAAGC GCUUUCU G | 59 | MIMAT0002837 AAAGUGCA UCCUUUUA GAGGUU | 90 |
| miR-520b | MI0003155 CCCUCUACAGGGAAGCGC UUUCUGUUGUCUGAAAGA AAAGAAAGUGCUUCCUUU UAGAGGG | 31 | — | | MIMAT0002843 AAAGUGCU UCCUUUUA GAGGG | 91 |
| miR-519c | MI0003148 UCUCAGCCUGUGACCCUC UAGAGGGAAGCGCUUUCU GUUGUCUGAAAGAAAAGA AAGUGCAUCUUUUUAGAG GAUUACAGUUUGAGA | 32 | MIMAT0002831 CUCUAGA GGGAAGC GCUUUCU G | 60 | MIMAT0002832 AAAGUGCA UCUUUUA GAGGAU | 92 |

TABLE 1-continued

| miRNA | miRBase Accession No./ Precursor Sequence (stem-loop) (5'-3') | SEQ ID NO: | miRBase Accession No./ 5p Mature Sequence ID and Sequence | SEQ ID NO: | miRBase Accession No./ 3p Mature Sequence ID and Sequence | SEQ ID NO: |
|---|---|---|---|---|---|---|
| miR-520f | MI0003146 UCUCAGGCUGUGACCCUC UAAAGGGAAGCGCUUUCU GUGGUCAGAAAGAAAAGC AAGUGCUUCCUUUUAGAG GGUUACCGUUUGGGA | 33 | MIMAT0026609 CCUCUAA AGGGAAG CGCUUUC U | 61 | MIMAT0002830 AAGUGCUU CCUUUUAG AGGGUU | 93 |
| miR-498 | MI0003142 AACCCUCCUUGGGAAGUG AAGCUCAGGCUGUGAUUU CAAGCCAGGGGGCGUUUU UCUAUAACUGGAUGAAAA GCACCUCCAGAGCUUGAA GCUCACAGUUUGAGAGCA AUCGUCUAAGGAAGUU | 34 | MIMAT0002824 UUUCAAG CCAGGGG GCGUUUU UC | 62 | — | |
| miR-520c | MI0003158 UCUCAGGCUGUCGUCCUC UAGAGGGAAGCACUUUCU GUUGUCUGAAAGAAAAGA AAGUGCUUCCUUUUAGAG GGUUACCGUUUGAGA | 35 | MIMAT0005455 CUCUAGA GGGAAGC ACUUUCU G | 63 | MIMAT0002846 AAAGUGCU UCCUUUUA GAGGGU | 94 |

In some embodiments, the step of measuring the expression or presence of the C19MC miRNA(s) can be performed by contacting a post-natal tissue or post-natal bodily fluid sample with a probe configured to specifically bind to a C19MC miRNA and measuring the amount, either qualitatively or quantitatively, of specific binding that occurred. In embodiments, the amount of specific binding that occurred can be compared to a suitable control. Suitable controls will be appreciated by those of skill in the art. In embodiments, the probe can be a DNA or RNA probe that can have a fully or partially complimentary sequence to a miRNA shown in Table 1. In some embodiments, the probe can be configured to bind a seed sequence of a miRNA shown in Table 1 (underlined regions correspond to the seed regions). In embodiments, the sample can be from an IH tumor. Specific binding of the probe and the C19MC miRNA present in the sample can be evaluated by techniques, including but not limited to, polymerase chain reaction (PCR), reverse-transcription PCR (RT-PCR), quantitative PCR (qPCR), RT-qPCR, arrays (including microarrays), multiplex miRNA profiling, northern blotting, and in situ hybridization. In some embodiments, the miRNAs present in the sample can be concentrated and/or extracted from the tissue or bodily fluid prior to contacting a probe. Suitable extraction and/or concentration techniques will be appreciated by those of skill in the art.

In some embodiments, the step of measuring the expression and/or presence of the C19MC miRNA(s) can be performed by small RNA sequencing (small RNA-seq) or other suitable sequencing based technique such as ultra-low-input and single-cell RNA-seq. In some embodiments, the miRNAs present in the sample can be concentrated and/or extracted from the tissue or bodily fluid prior to being subjected to a sequencing technique. Suitable extraction and/or concentration techniques will be appreciated by those of skill in the art. In embodiments, the amount of C19MC miRNA expression and or molecules in the sample can be compared to a suitable control. Suitable controls will be appreciated by those of skill in the art.

In some embodiments, the step of measuring the expression and/or presence of the C19MC miRNA(s) can be followed by reducing C19MC miRNA amount and/or C19MC miRNA expression and/or CpG methylation in the promoter region of the C19MC miRNAs in a subject in need thereof. The expression and/or presence of the C19MC miRNA(s) can be reduced in the subject by administering the subject an effective amount of a C19MC miRNA inhibitor. Suitable C19MC miRNA inhibitors include but are not limited to small molecule chemicals and compounds and biologic compounds (including, but not limited to proteins, aptamers, antibodies, and polynucleotides) and pharmaceutical formulations thereof. Some examples of suitable C19MC miRNA inhibitors include antisense microRNA capable of binding the C19MC miRNA, CRISPRi or KRAB-dCas9 system, aptamers, miRNA inhibitors, propranolol, non-selective beta adrenergic receptor blockers, mTOR inhibitors and/or MAPK inhibitors.

In embodiments, the methods can include the steps of obtaining a post-natal tissue or bodily fluid sample from a subject and measuring the levels of C19MC, active transcription from the upstream promoter region or CpG methylation on the upstream promoter region of the C19MC miRNAs in the sample. As used herein the upstream promoter region of the C19MC miRNAs refers to SEQ ID NO: 95 or the region on chromosome 19 from nucleotide 54150726 to nucleotide 54151735 of CpG island 86.

Suitable methods of measuring active transcription form the upstream promoter region include, but are not limited to, PCR, quantitative RT-PCR and relative RT-PCR.

Suitable methods of measuring DNA methylation include, but are not limited to, bisulfite sequencing and HpaII sensitivity analysis.

In some embodiments, the assays provided herein can be used to diagnose and/or prognose IH or other post-natal diseases or disorders, including but not limited to infantile hepatic hemangioma, infantile brain tumors such as primitive neuroectodermal tumors (PNET), medulloblastoma, cerebellar PNET, and supratentorial PNET. In some embodiments, the amount and/or expression of one or more C19MC miRNAs in the post-natal sample can be greater than a wild-type, normal, or un-diseased control. In some embodiments, the amount and/or expression of one or more C19MC miRNAs in the post-natal sample can be about 10% to 500% or more increased as compared to the amount and/or expression in a wild-type, normal, or un-diseased control. In embodiments, a diagnosis of IH, infantile hepatic hemangioma, infantile brain tumors such as primitive neuroectodermal tumors (PNET), medulloblastoma, cerebellar PNET and/or supratentorial PNET can be made when the amount and/or expression of one or more C19MC miRNAs in the post-natal sample is greater than a wild-type, normal, or un-diseased control. In embodiments, a diagnosis of IH, infantile hepatic hemangioma, infantile brain tumors such as primitive neuroectodermal tumors (PNET), medulloblastoma, cerebellar PNET and/or supratentorial PNET can be made when the amount and/or expression of one or more C19MC miRNAs in the post-natal sample is about 10% to 500% or more increased as compared to the amount and/or expression in a wild-type, normal, or un-diseased control.

In some embodiments, the amount of CpG methylation in the upstream promoter region of the C19MC miRNAs can be less than a wild-type, normal, or un-diseased control. In some embodiments, the amount of CpG methylation in the upstream promoter region of the C19MC miRNAs in the post-natal sample can be about 10% to 500% or more decreased as compared to the amount and/or expression in a wild-type, normal, or un-diseased control. In some embodiments, a diagnosis or prognosis of IH or other disease can be made when the amount of CpG methylation in the upstream promoter region of the C19MC miRNAs is less than a wild-type, normal, or un-diseased control. In some embodiments, a diagnosis or prognosis of IH or other disease can be made when the amount of CpG methylation in the upstream promoter region of the C19MC miRNAs is about 10% to 500% or more decreased as compared to the amount and/or expression in a wild-type, normal, or un-diseased control.

Methods of Treating a C19MC microRNA Disease or Disorder

Also provided herein are methods of upregulating and reducing C19MC miRNA amount and/or C19MC miRNA expression and/or CpG methylation in the promoter region of the C19MC miRNAs in a cell, population thereof, and/or in a subject in need thereof. By reducing the c19MC miRNA amount and/or expression by targeting specific miRNAs within the C19MC or by using CRISPR to suppress/activate the expression of C19MC and/or CpG methylation in the promoter region of the C19MC miRNAs, a C19MC miRNA mediated disease and/or symptom thereof can be treated. To inhibit C19MC the CRISPRi or KRAB-dCas9 system (CRISPR knockout screening can be used, which outperforms shRNA and CRISPRi in identifying essential genes. Bastiaan Evers, Katarzyna Jastrzebski, Jeroen P M Heijmans, Wipawadee Grernrum, Roderick L Beijersbergen & Rene Bernards Nature Biotechnology 34, 631-633 (2016). These systems can be used with gRNA designed to target highly conserved exons 1-37 described in C19MC microRNAs are processed from introns of large PoI-II, non-protein-coding transcripts. Bortolin-Cavaillé ML1, Dance M, Weber M, Cavaillé J. Nucleic Acids Res. 2009 June; 37(10):3464-73. To activate C19MC the CRISPR/Cas9 SAM system and the following gRNAs can be used: #759 5' CACCG-CAAATCCTAGGCCTGCCCTG (SEQ ID NO: 96) or #620 5' CACCGGTGAGCTGATGATCGCTCCA (SEQ ID NO: 97). AAV virus, or in vitro transcribed mRNA can be used to deliver the different CRISPR components.

Such C19MC miRNA mediated diseases include but are not limited to, IH, infantile hepatic hemangioma, infantile brain tumors such as primitive neuroectodermal tumors (PNET), medulloblastoma, cerebellar PNET, and supratentorial PNET, choriocarcinoma, preeclampsia, intrauterine growth restriction. The methods can include the step of administering to a cell, population of cells, or a subject in need thereof an amount of a C19MC miRNA inhibitor. Suitable C19MC miRNA inhibitors include but are not limited to small molecule chemicals and compounds and biologic compounds (including, but not limited to proteins, aptamers, antibodies, and polynucleotides) and pharmaceutical formulations thereof. Some examples of suitable C19MC miRNA inhibitors include antisense microRNA capable of binding the C19MC miRNA, CRISPRi or KRAB-dCas9 system, aptamers, miRNA inhibitors, propranolol, non-selective beta adrenergic receptor blockers, mTOR inhibitors and/or MAPK inhibitors.

In some embodiments, the inhibitor can decreased the amount of CpG methylation in the upstream C19MC miRNA promoter region as compared to a normal, wild-type, and/or un-diseased control. In some embodiments, the inhibitor can reduce the transcription of one or more C19MC miRNAs. In some embodiments, the inhibitor can reduce the amount of one or more C19MC miRNAs present in a cell, population of cells, or subject in need thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 2:
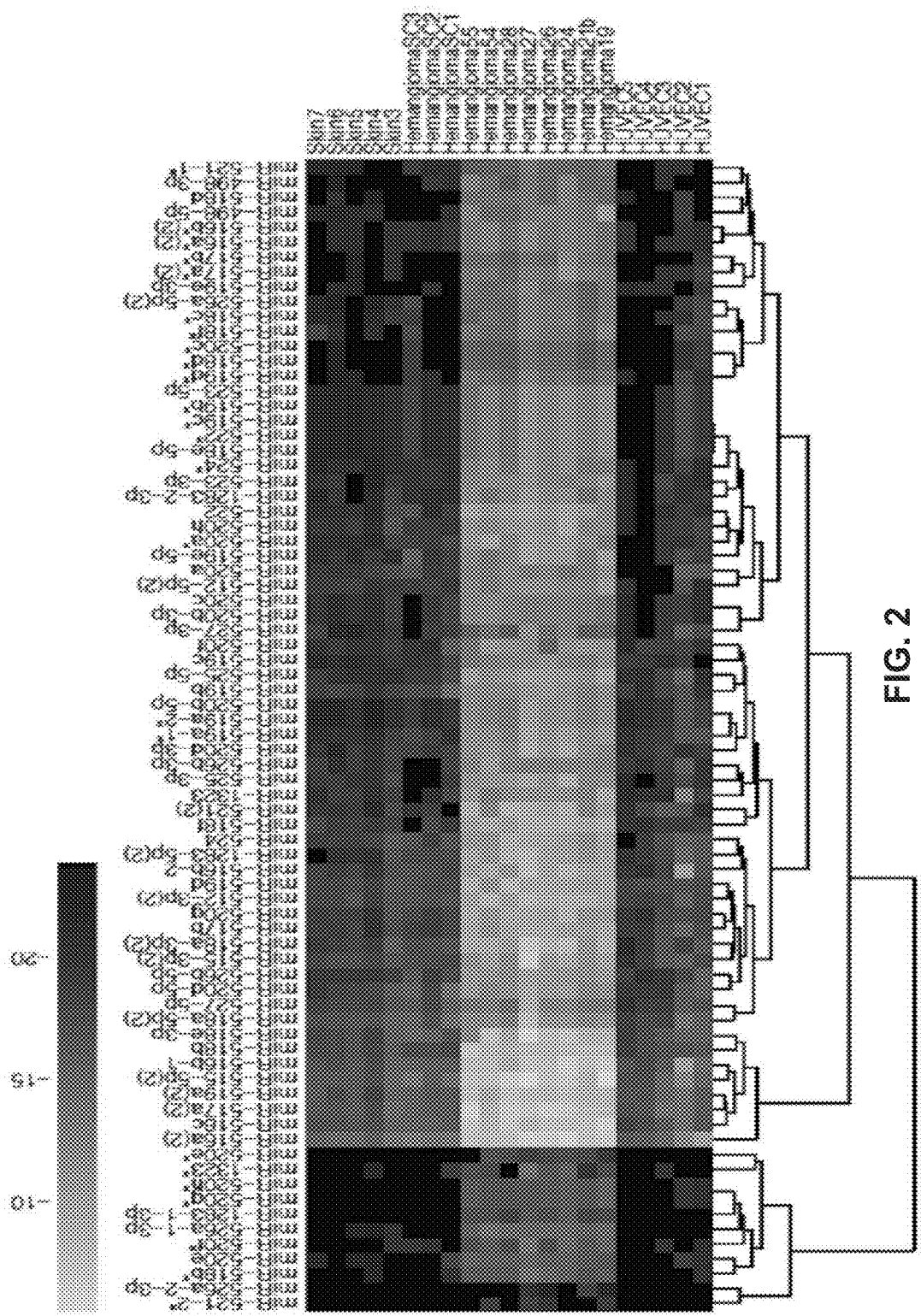
FIG. 2 shows results from a comparison of individual miRNAs of the principally altered Cluster-hsa-mir-498 (C19mc) in Hemangioma samples compared to Skin, HUVECs and HemSC. The heatmap shown in FIG. 2 demonstrates the average change in miRNA expression in the 4 groups analyzed. Graded colors are proportional to expression levels expressed as Log 2 read frequency (yellow (light gray) high, blue (dark gray) low, and black absent).

To identify differentially expressed miRNAs in IH, we performed small RNA sequencing of eight different samples taken from IH tissues and five normal skin tissues for control. We also performed small RNA sequencing of 5 samples of Human Umbilical Vein Endothelial Cells (HUVECs) and 3 samples of Hemangioma Stem Cells (HemSc) isolated from IH tissues as previously described (Khan, et al., J. Clin. Invest. 118:7, 2592-9, 2008). Unsupervised hierarchical clustering of RNAseq data identified four distinct groups corresponding to the experimental groups (FIG. 1). IH samples showed significant upregulation of the miRNA-498 cluster also known as C19MC (FIG. 1) that contains 58 miRNA genes of which 77 were found to be significantly unregulated in IH samples but not in the normal skin sample, HemSc or HUVECs (FIG. 2). This novel finding is in agreement with previous studies that have identified similarities between IH and the placenta Numerous studies showed that C19MC is regulated by methylation. In order to test whether methylation is the reason behind its absent in HUVECs, HUVEC were treated with DNA methyltransferase inhibitor 5-azacytidine (5-aza) and quantified the expression of one member of the C19MC cluster randomly selected miR-519d, by RT-PCR. HUVEC treated with 5-aza showed significant increase (>70 fold) in miR-519d expression.

These data demonstrate for the first time that Infantile Hemangioma exhibit increase in C19MC expression, which may be due to reduced methylation.

Example 2

Figure 3:
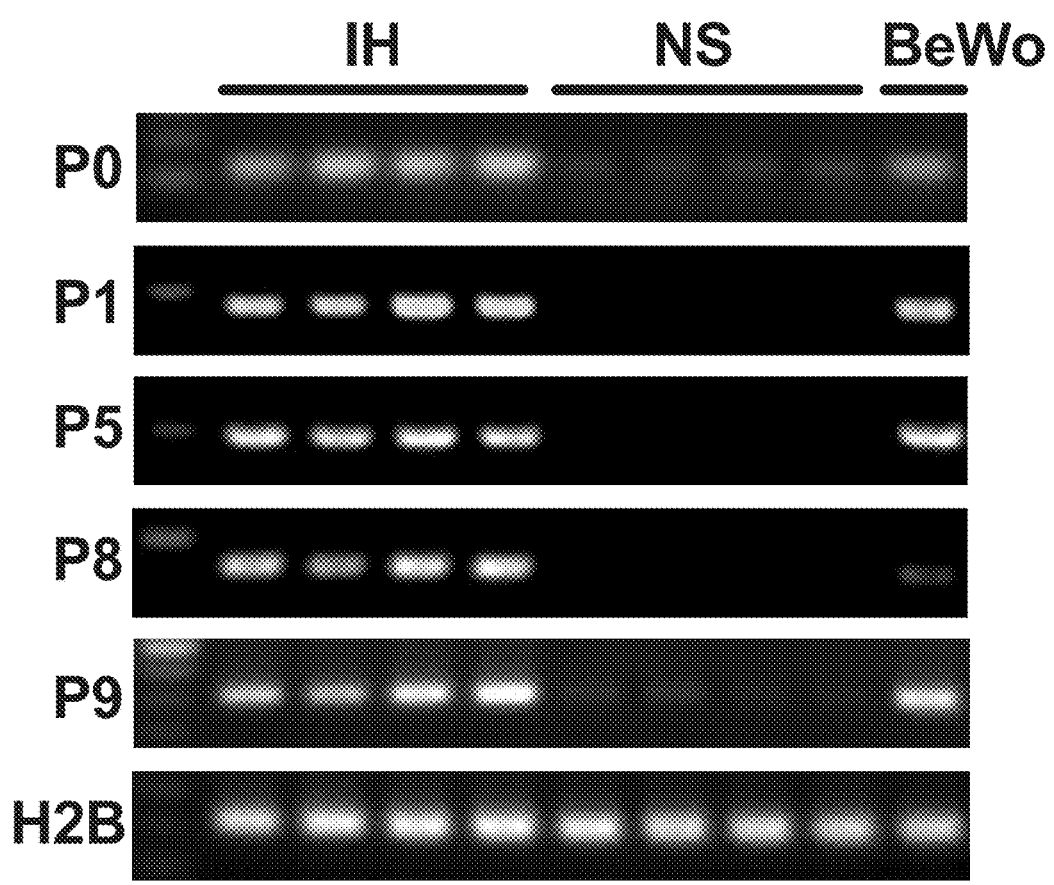
FIG. 3 shows active transcription starting from upstream CpG-rich island promoter region in IH samples and BeWo cells, but not NS. RT-PCR and primer sets that were designed to amplify regions downstream of the CpG-island previously described (Noguer-Dance M, Abu-Amero S, Al-Khtib M, Lefevre A, Coullin P, Moore G E, Cavaille J. The primate-specific microrna gene cluster (c19mc) is imprinted in the placenta. *Human molecular genetics.* 2010; 19:3566-3582) was performed. Trophoblast-derived choriocarcinoma BeWo cell line that endogenously express C19MC was used for positive control.

The data shown in Example 1 can demonstrate a significant upregulation in chromosome 19 miRNA cluster (C19MC) in IH. This cluster of miRNAs is placenta and primate specific (Noguer-Dance, Hum. Mol. Genet. 19:18, 3566-3582, 2010; Mouillet, et al., Am. J. Obstet. Gynecol. 213:4, S163-S172, 2015). C19MC is controlled by methylation of an upstream CpG rich promoter region that comprises a transcription start site located ~17 kb upstream of the first miRNA gene. To test whether this upstream CpG-rich island is transcriptionally active in IH, we performed RT-PCR using primer sets that were designed to amplify regions downstream of the CpG-island previously described (Noguer-Dance M, Abu-Amero S, Al-Khtib M, Lefevre A, Coullin P, Moore G E, Cavaille J. The primate-specific microrna gene cluster (c19mc) is imprinted in the placenta. Human molecular genetics. 2010; 19:3566-3582). We also used the trophoblast-derived choriocarcinoma BeWo cell line that endogenously express C19MC as positive control. IH samples and BeWo cells, but not NS, showed active transcription starting at the ~17 kb upstream C19MC CpG-related promoter region (FIG. 3).

Figure 4:
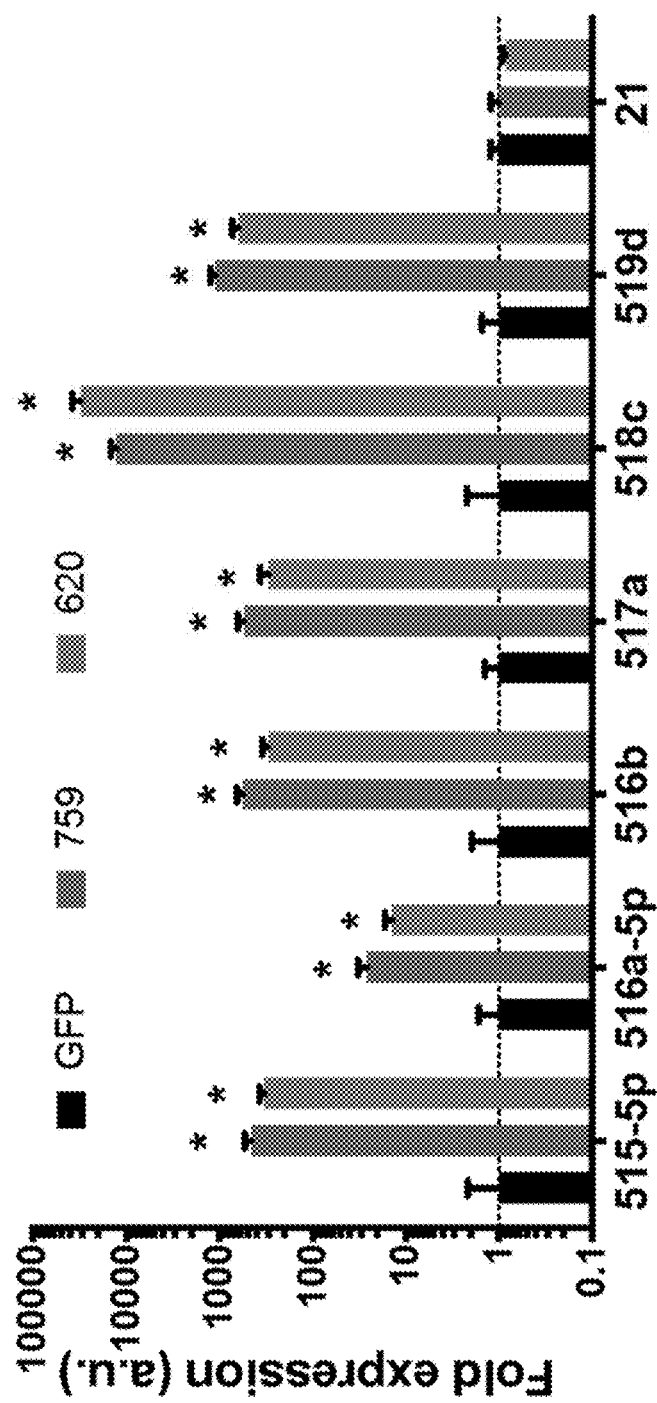
FIG. 4 shows results of transient transfection of HEK293 cells with two different guide RNA sequences (gRNA759 and gRNA620) and the CRISPR/Cas9 SAM system >10-fold increase in the expression of 6 randomly selected miRNAs of the C19MC, but not of miRNA miR-21 a non-member of the C19MC cluster that was used as a control (FIG. 3).

Although C19MC has been implicated in cellular processes such as proliferation, invasion and differentiation, it is role in the pathogenesis of IH has never been evaluated (Mouillet, et al., Am. J. Obstet. Gynecol. 213:4, S163-S172, 2015). To evaluate the direct effects of C19MC on endothelial cells we will induce its expression using a modified CRISPR/Cas 9 Synergistic Activation Mediator (SAM) system that utilizes an engineered protein complex for the transcriptional activation of C19MC. This protein complex has three components: 1) a nucleolytically inactive Cas 9-VP64 fusion protein; 2) sgRNA that incorporates two MS2 RNA aptamers on its tetraloop and stemloop and 3) an MS2-P65-HSF1 activation helper protein (Konermann, et al., Nature 517:7536, 583-8, 2014). This unique CRISPR/Cas 9 design leverages the synergistic activity of three distinct activation domains to significantly increase expression of any target Gene. Id. Transient transfection of HEK293 cells with 2 different gRNA (gRNA759 and gRMA620) and the CRISPR/Cas9 SAM system showed >10-fold increase in the expression of 6 randomly selected miRNAs of the C19MC, but not of miRNA miR-21 a non-member of the C19MC cluster that was used as a control (FIG. 4). To further confirm the specificity and the extent of overexpression of the entire C19MC cluster we performed small RNA sequencing analysis of HEK293 cells transiently transfected with gRNA759 and CRISPR/Cas 9 SAM compared to cells transfected with CRISPR/Cas9 SAM with an empty gRNA plasmid. Out of the sixty-nine significantly changed (thresholds: 2-fold, p<0.01) miRNAs, fifty-eight belonged to the C19MC cluster, which were all upregulated by 5- to 900-fold (Table 2). Table 2 shows results from a small RNA sequencing analysis of HEK293 cells transiently transfected with gRNA759 and CRISPR/Cas9 SAM compared to cells transfected with CRISPR/Cas9 SAM with an empty gRNA plasmid. These data demonstrate that the CRISPR/Cas9 SAM system can be used to selectively and effectively upregulate the entire C19MC cluster that spans over 100 Kb.

TABLE 2

| miRNA | 759gRNA CRISPR/Cas9 | Control | Fold Change | P Value |
|---|---|---|---|---|
| 525-3p(1) | 0.004799% | 0.000005% | 900.5 | 6.0011E−04 |
| 520e-3p(1) | 0.003716% | 0.000005% | 692.4 | 4.9271E−05 |
| 518c-3p(1) | 0.024946% | 0.000040% | 631.2 | 1.1291E−06 |
| 520a-3p(1) | 0.003212% | 0.000005% | 597.8 | 9.0259E−05 |
| 519e-5p(1) | 0.003097% | 0.000005% | 568.3 | 5.9996E−04 |
| 526b-5p(1) | 0.017139% | 0.000040% | 432.9 | 3.5435E−06 |
| 517STAR(3) | 0.002118% | 0.000006% | 379.7 | 3.0914E−04 |
| 512-3p(2) | 0.082218% | 0.000245% | 335.8 | 1.2440E−06 |
| 515(2) | 0.046566% | 0.000144% | 322.4 | 2.6157E−05 |
| 515STAR(2) | 0.017935% | 0.000057% | 315.1 | 1.2836E−04 |
| 520d-3p(1) | 0.001744% | 0.000006% | 306.1 | 1.8208E−04 |
| 885(1) | 0.001702% | 0.000006% | 301.8 | 4.7969E−04 |
| 519c-3p(1) | 0.019011% | 0.000073% | 260.2 | 1.0356E−06 |
| 518b-3p(1) | 0.014500% | 0.000057% | 254.5 | 6.3584E−06 |
| 512-5p(2) | 0.019217% | 0.000076% | 254.1 | 2.0160E−06 |
| 518a-1-3p(1) | 0.001476% | 0.000006% | 251.1 | 1.1268E−04 |
| 518a-2-3p(1) | 0.001476% | 0.000006% | 251.1 | 1.1268E−04 |
| 519b-3p(1) | 0.005728% | 0.000023% | 249.8 | 2.4825E−06 |
| 498(1) | 0.021764% | 0.000093% | 234.1 | 3.3188E−06 |
| 520e-5p(1) | 0.001279% | 0.000006% | 214.3 | 9.1338E−05 |
| 525-5p(1) | 0.018235% | 0.000090% | 202.2 | 2.8213E−06 |
| 519e-3p(1) | 0.001049% | 0.000006% | 168.5 | 3.1017E−04 |
| 517a(2) | 0.037037% | 0.000224% | 165.6 | 1.7670E−05 |
| 518d-3p(1) | 0.006366% | 0.000039% | 162.8 | 9.1901E−06 |
| 518c-5p(1) | 0.000991% | 0.000006% | 161.5 | 3.4919E−04 |
| 518d-5p(5) | 0.011081% | 0.000071% | 155.1 | 9.2224E−06 |
| 498STAR(1) | 0.000943% | 0.000006% | 150.3 | 4.7998E−04 |
| 524STAR(1) | 0.000936% | 0.000006% | 148.0 | 2.7901E-03 |
| 519d(1) | 0.020602% | 0.000141% | 145.9 | 2.5891E−05 |
| 1323(1) | 0.037557% | 0.000260% | 144.3 | 5.6153E−07 |
| 518b-5p(1) | 0.000905% | 0.000006% | 142.9 | 3.2734E−04 |
| 526a-1-3p(1) | 0.000849% | 0.000006% | 131.5 | 3.0958E−04 |
| 520f-5p(1) | 0.000829% | 0.000007% | 126.2 | 4.0502E−04 |
| 1270(2) | 0.000784% | 0.000006% | 123.3 | 3.4036E-03 |
| 520g-3p(2) | 0.015097% | 0.000127% | 119.0 | 9.9301E−06 |
| 518e-5p(5) | 0.013503% | 0.000122% | 110.8 | 5.5705E−06 |
| 524(1) | 0.049101% | 0.000467% | 105.3 | 4.4260E−05 |
| 520f-3p(1) | 0.063792% | 0.000620% | 102.9 | 1.0864E−05 |
| 516b(2) | 0.020732% | 0.000208% | 99.9 | 2.3803E−05 |
| 520a-5p(1) | 0.035758% | 0.000377% | 94.8 | 1.9058E−05 |
| 519dSTAR(1) | 0.000657% | 0.000007% | 94.4 | 6.5445E−04 |
| 520b-3p(2) | 0.013027% | 0.000142% | 91.8 | 4.8170E−05 |
| 526b-3p(1) | 0.005214% | 0.000058% | 90.3 | 1.4756E−05 |
| 521-2STAR(1) | 0.000635% | 0.000007% | 89.9 | 3.5900E-03 |
| 517b(1) | 0.008088% | 0.000090% | 89.7 | 5.4469E−06 |
| 523-3p(1) | 0.004434% | 0.000057% | 77.7 | 7.6582E−06 |
| 520g-5p(2) | 0.001844% | 0.000025% | 73.2 | 7.4178E−05 |
| 518f-3p(1) | 0.012531% | 0.000187% | 67.0 | 3.6687E−05 |
| 520d-5p(1) | 0.025045% | 0.000432% | 58.0 | 8.8336E−04 |
| 516STAR(4) | 0.000433% | 0.000008% | 53.1 | 5.0960E-03 |
| 518e-3p(1) | 0.002287% | 0.000061% | 37.4 | 8.3481E−04 |
| 519a-1-5p(1) | 0.003783% | 0.000108% | 35.1 | 6.9123E−05 |
| 1283-2-3p(1) | 0.000763% | 0.000029% | 26.6 | 1.8499E-03 |
| 1283-5p(2) | 0.007164% | 0.000342% | 20.9 | 5.3322E−05 |
| 519a-2-5p(2) | 0.002844% | 0.000137% | 20.7 | 3.4599E−05 |
| 518a-5p(3) | 0.007050% | 0.000397% | 17.7 | 4.1041E−04 |
| 133a(2) | 0.002260% | 0.000205% | 11.0 | 6.6827E-03 |
| 519a-3p(2) | 0.005371% | 0.000487% | 11.0 | 4.9883E-03 |
| 522-3p(1) | 0.002773% | 0.000328% | 8.5 | 2.8108E-03 |
| 489(1) | 0.001916% | 0.000281% | 6.8 | 5.6026E−04 |
| 516a(2) | 0.012263% | 0.001935% | 6.3 | 1.8791E-03 |
| 539(1) | 0.001254% | 0.000216% | 5.8 | 4.3859E-03 |
| 449c(1) | 0.009596% | 0.001836% | 5.2 | 4.1839E-03 |
| 135bSTAR(1) | 0.000513% | 0.000100% | 5.1 | 9.9998E-03 |
| 449b(1) | 0.003243% | 0.000639% | 5.1 | 8.5672E−04 |
| 377(1) | 0.002802% | 0.000709% | 4.0 | 7.5486E-03 |
| 708STAR(1) | 0.013535% | 0.004130% | 3.3 | 4.3404E-03 |
| 588-3p(1) | 0.000037% | 0.000430% | −11.7 | 7.4211E-03 |
| 2116STAR(1) | 0.000025% | 0.000343% | −13.7 | 5.9438E-03 |

We claim:

1. A method for treating infantile hemangioma (IH), infantile hepatic hemangioma, infantile brain tumor, choriocarcinoma, preeclampsia, or intrauterine growth restriction, the method comprising:
   obtaining a sample of post-natal tissue or post-natal bodily fluid from a subject; and
   contacting the post-natal tissue or bodily fluid sample or component thereof with a probe configured to specifically bind to the C19MC miRNA, detecting the amount of specific binding of the probe and the C19MC miRNA in the sample, and measuring the amount or expression of C19MC miRNA in the sample, and detecting an increase in the expression of the C19MC miRNA in the sample as compared to a wild-type, normal, or un-diseased control;
   administering to the subject a C19MC miRNA inhibitor, wherein the C19MC miRNA inhibitor is an antisense microRNA capable of specifically binding a C19MC miRNA, wherein the antisense microRNA is capable of decreasing the amount of the C19MC miRNA in the subject,
   and wherein the C19MC miRNA is selected from the group consisting of: miR-516a, miR518c, miR-517a, miR-519a-1, miR-515-1, miR-516b-1, miR-518b, miR-518e, miR-518a-1, miR-515-2, miR-512-1, miR-518f, miR-1283-1, miR-519d, miR-517-b, miR-521-2, miR-524, miR-520g, miR-525, mir-520d, miR-526b, miR519e, miR-1323, miR-522, miR-519a-2, miR-520a, miR-527, miR-523, miR-520h, miR-519b, miR-520b, mir-519c, miR-520f, miR-498, miR-520c, and combinations thereof.

2. A method for treating infantile hemangioma (IH), infantile hepatic hemangioma, infantile brain tumor, choriocarcinoma, preeclampsia, or intrauterine growth restriction, the method comprising:
   obtaining a sample of post-natal tissue or post-natal bodily fluid from a subject; and
   contacting a post-natal tissue or bodily fluid sample or component thereof with a probe configured to specifically bind to the C19MC miRNA, detecting the amount of specific binding of the probe and the C19MC miRNA in the sample, and measuring CpG methylation in the C19MC miRNA upstream promoter region in the sample, and detecting a decrease in CpG methylation in the upstream C19MC miRNA promoter region as compared to a wild-type, normal, or un-diseased control;
   administering to the subject a C19MC miRNA inhibitor, wherein the C19MC miRNA inhibitor is an antisense microRNA capable of specifically binding a C19MC miRNA, wherein the antisense microRNA is capable of decreasing the amount of the C19MC miRNA in the subject,
   and wherein the C19MC miRNA is selected from the group consisting of: miR-516a, miR518c, miR-517a, miR-519a-1, miR-515-1, miR-516b-1, miR-518b, miR-518e, miR-518a-1, miR-515-2, miR-512-1, miR-518f, miR-1283-1, miR-519d, miR-517-b, miR-521-2, miR-524, miR-520g, miR-525, mir-520d, miR-526b, miR519e, miR-1323, miR-522, miR-519a-2, miR-520a, miR-527, miR-523, miR-520h, miR-519b, miR-520b, mir-519c, miR-520f, miR-498, miR-520c, and combinations thereof.

3. The method of claim 1, wherein IH, infantile hepatic hemangioma, or infantile brain tumor is diagnosed in the subject when the C19MC miRNA measured has an increased amount or expression as compared to a wild-type, normal, or un-diseased control.

4. The method of claim 2, wherein IH, infantile hepatic hemangioma, or infantile brain tumor is diagnosed in the subject when the CpG methylation in the upstream C19MC miRNA promoter region is decreased as compared to a wild-type, normal, or un-diseased control.

5. The method of claim 1, wherein the C19MC miRNA has a precursor sequence that is 90% to 100% identical to any one of SEQ ID NOs: 1-35.

6. The method of claim 2, wherein the C19MC miRNA has a precursor sequence that is 90% to 100% identical to any one of SEQ ID NOs: 1-35.

* * * * *